United States Patent
Kim et al.

(10) Patent No.: US 11,873,517 B2
(45) Date of Patent: *Jan. 16, 2024

(54) CANDIDA TROPICALIS STRAIN HAVING IMPROVED TOLERANCE TO THE CYTOTOXICITY OF SUBSTRATES, AND METHOD FOR PRODUCING DICARBOXYLIC ACID USING SAME

(71) Applicant: Korea University Research and Business Foundation, Seoul (KR)

(72) Inventors: Kyoung Heon Kim, Seoul (KR); Thirumalaisamy Babu, Seoul (KR); Do Hyoung Kim, Yongin-si (KR); Jong Hwa Lee, Daejeon (KR); Jung Moo Lee, Daejeon (KR); Ho Chang Lee, Daejeon (KR); Sung Ho Oh, Sejong (KR); Su Han Kim, Daejeon (KR); Chang Seok Hyun, Daejeon (KR)

(73) Assignee: Korea University Research and Business Foundation, Seoul (KR)

( * ) Notice: Subject to any disclaimer, the term of this patent is extended or adjusted under 35 U.S.C. 154(b) by 268 days.

This patent is subject to a terminal disclaimer.

(21) Appl. No.: 17/299,194

(22) PCT Filed: Dec. 4, 2019

(86) PCT No.: PCT/KR2019/017044
§ 371 (c)(1),
(2) Date: Jun. 2, 2021

(87) PCT Pub. No.: WO2020/116941
PCT Pub. Date: Jun. 11, 2020

(65) Prior Publication Data
US 2022/0033790 A1    Feb. 3, 2022

(30) Foreign Application Priority Data
Dec. 4, 2018 (KR) .................. 10-2018-0154372

(51) Int. Cl.
*C12N 9/20* (2006.01)
*C07K 14/40* (2006.01)
*C12P 7/44* (2006.01)

(52) U.S. Cl.
CPC .............. *C12N 9/20* (2013.01); *C07K 14/40* (2013.01); *C12P 7/44* (2013.01); *C12Y 301/01003* (2013.01)

(58) Field of Classification Search
None
See application file for complete search history.

(56) References Cited

FOREIGN PATENT DOCUMENTS

KR    20170048763    *    5/2017

OTHER PUBLICATIONS

Accession MF924816. Aug. 12, 2018 (Year: 2018).*
Accession BEF18841. Oct. 5, 2017 (Year: 2017).*
Accession AEH89710. Jul. 27, 2006 (Year: 2006).*
Bornscheuer et al. Curr Protoc Protein Sci. Nov. 2011;Chapter 26:Unit26.7. (Year: 2011).*
Yoshikuni et al. Curr Opin Chem Biol. Apr. 2007; 11(2):233-9 (Year: 2007).*
KR20170048763. May 10, 2017. English translation. (Year: 2017).*
NCBI, Genbank Accession No. XM_002548456, *Candida tropicalis* MYA-3404 lipase 1 precursor (CTRG_02799), partial mRNA, Apr. 11, 2018, 3 pages.
NCBI, Genbank Accession No. XM_002548593, *Candida tropicalis* MYA-3404 very long-chain fatty acid transport protein (CTRG_02936), partial mRNA, Apr. 11, 2018, 3 pages.
NCBI, Genbank Accession No. XM_002548183, *Candida tropicalis* MYA-3404 multidrug resistance protein CDR1 (CTRG_02526), partial mRNA, Apr. 11, 2018, 4 pages.
Yue Fu, et al., "Cloning and characterization of a gene (LIP1) which encodes a lipase from the pathogenic yeast *Candida albicans*", Microbiology, 1997, vol. 143, pp. 331-340.
Zhiying Zou, et al., "Fatty Acid Transport in *Saccharomyces cerevisiae* Directed Mutagenesis of FAT1 Distinguishes the Biochemical Activities Associated With Fat1p", The Journal of Biological Chemistry, The American Society for Biochemistry and Molecular Biology, Inc., Jun. 2002, pp. 31062-31071, vol. 277, No. 34.
International Search Report for PCT/KR2019/017044 dated May 25, 2020 (PCT/ISA/210).
Communication dated Jul. 11, 2023, issued in Chinese Application No. 201980091207.5.

* cited by examiner

*Primary Examiner* — Christian L Fronda
(74) *Attorney, Agent, or Firm* — Sughrue Mion, PLLC

(57) ABSTRACT

The present invention relates to a *Candida tropicalis* cell line, which comprises a mutant gene, having improved tolerance for cytotoxicity of stromal cells, and a method for producing dicarboxylic acid using the *Candida tropicalis* cell line. The *Candida tropicalis* cell line for producing dicarboxylic acid developed according to the present invention has improved tolerance for existing stromal toxicity as well as significantly improved efficiency for producing dicarboxylic acid compared to existing cell lines, thus can be used in biological production of dicarboxylic acid and is expected to have high industrial utility.

7 Claims, 19 Drawing Sheets
Specification includes a Sequence Listing.

[Figure 1]
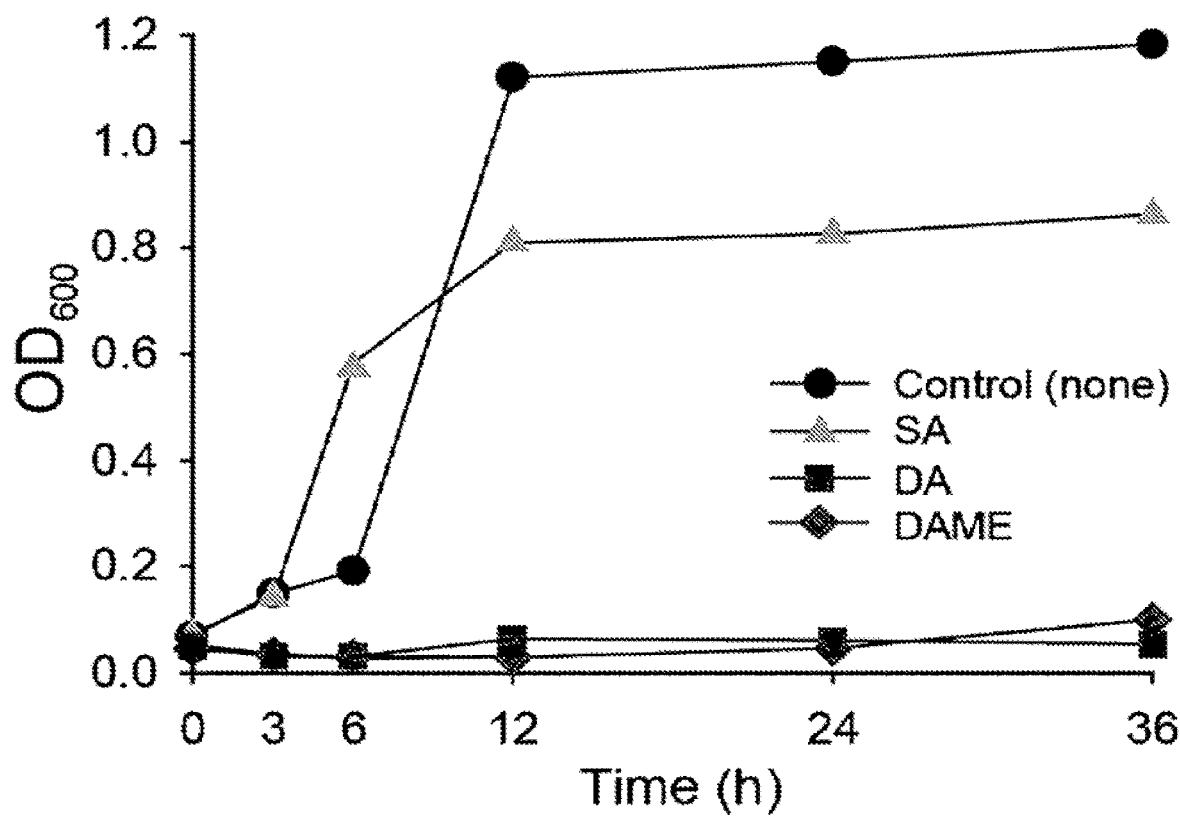

[Figure 2]
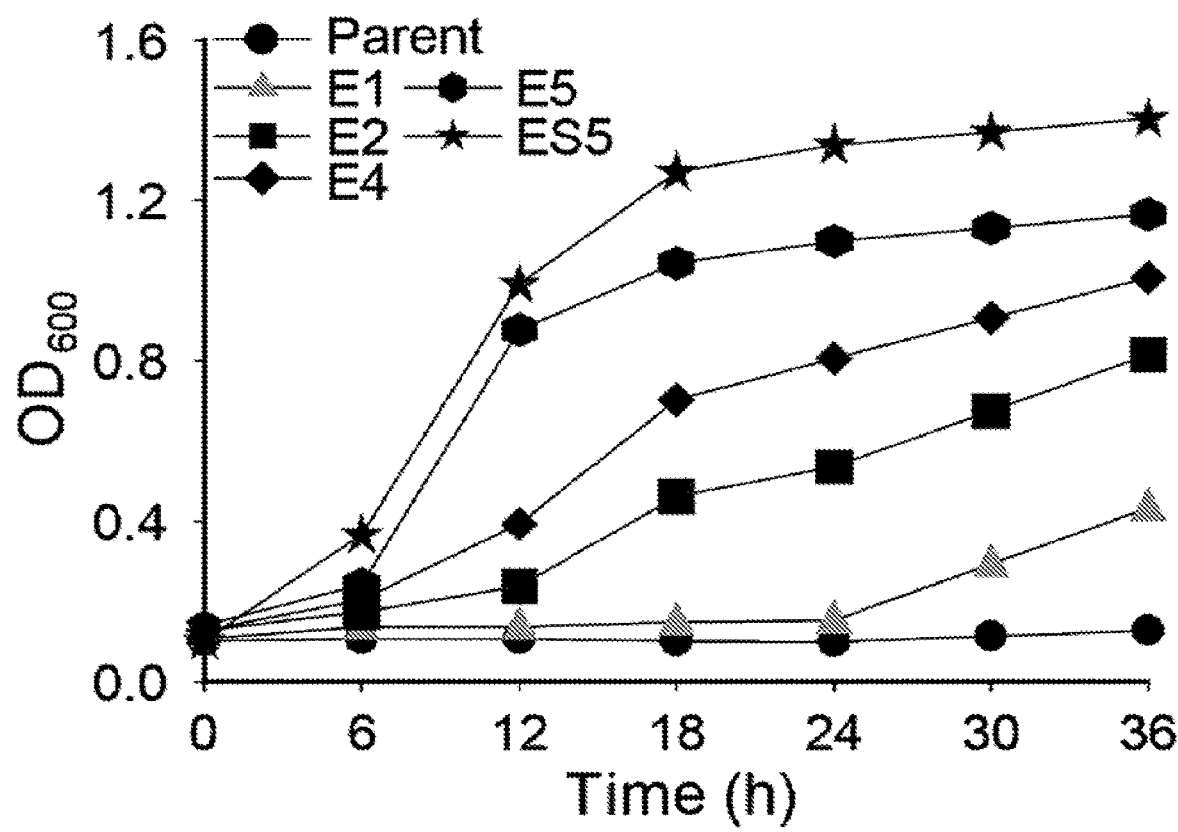

[Figure 3]
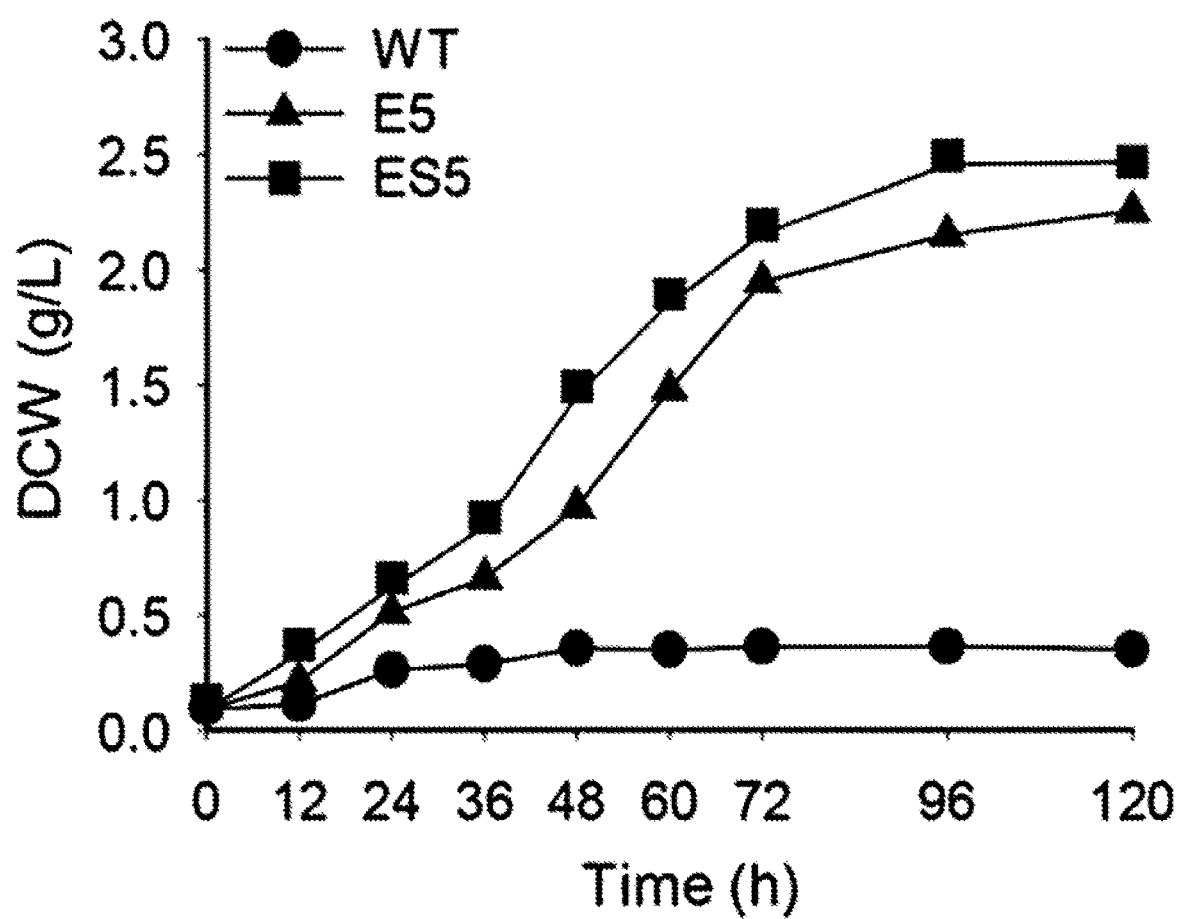

[Figure 4]
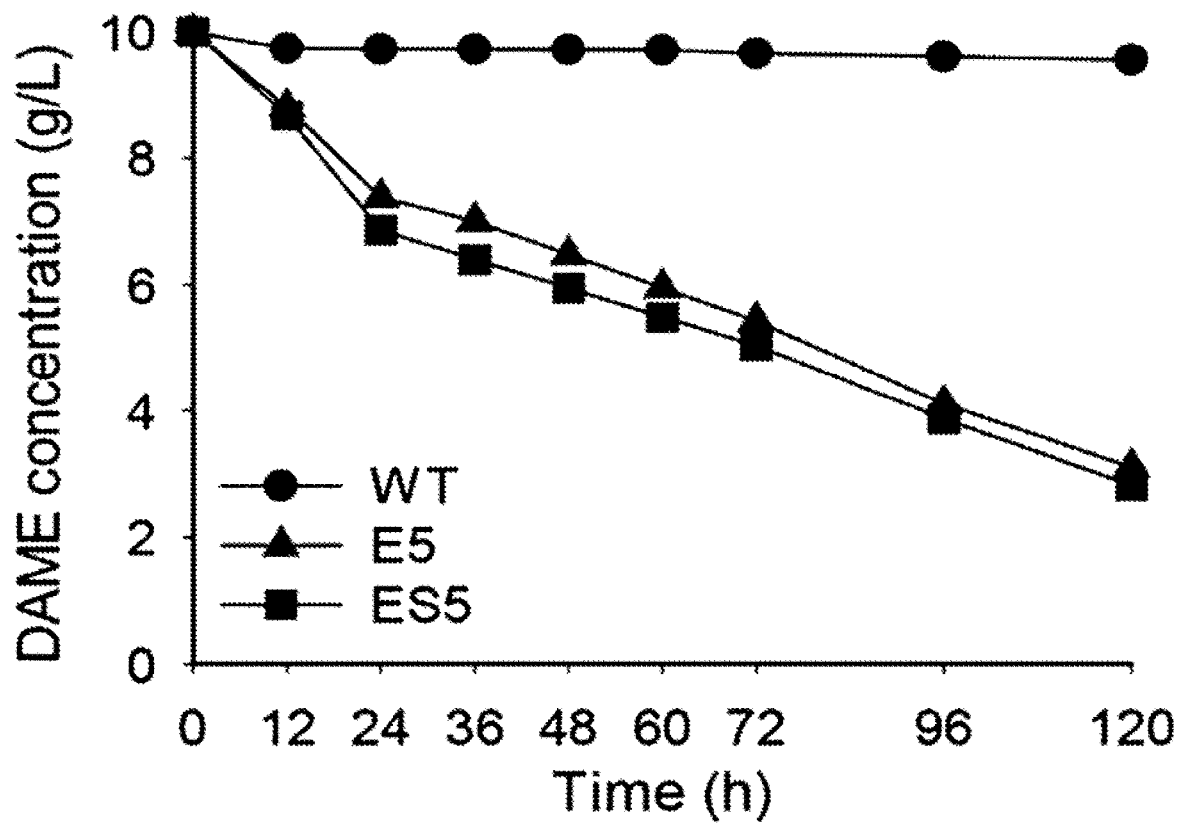

[Figure 5]
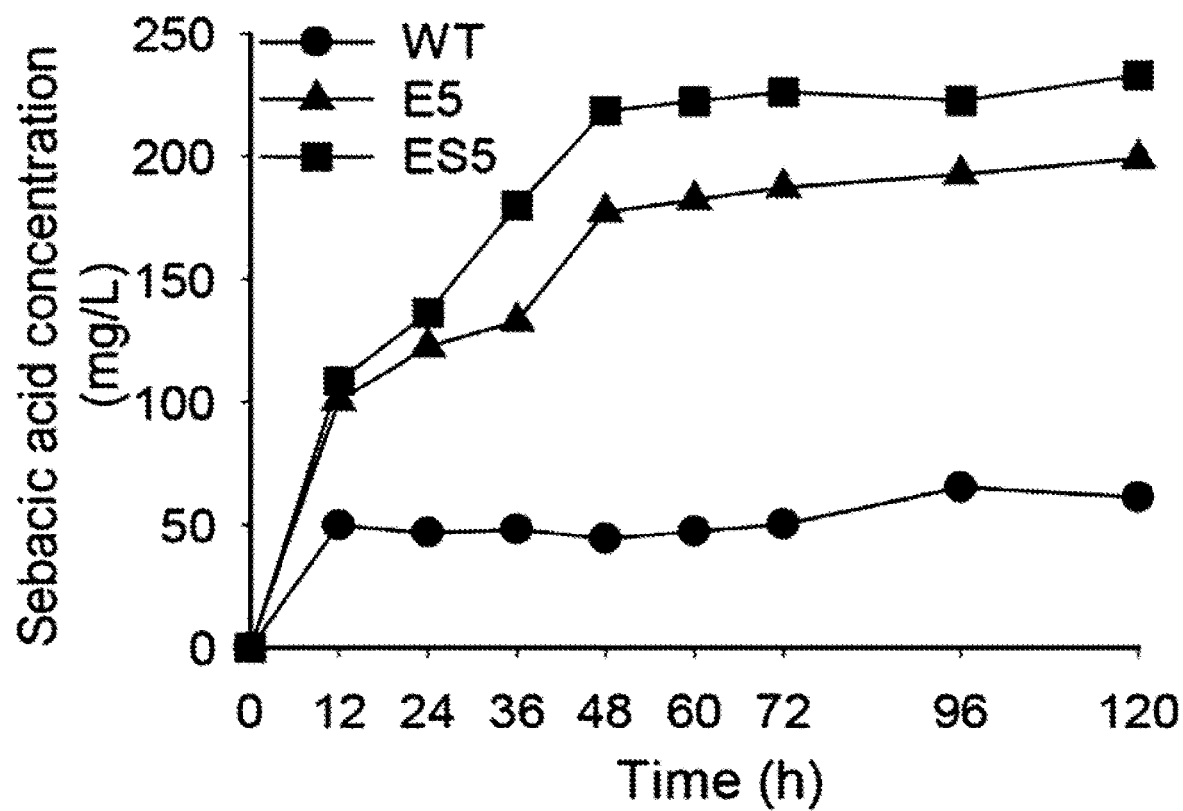

[Figure 6]
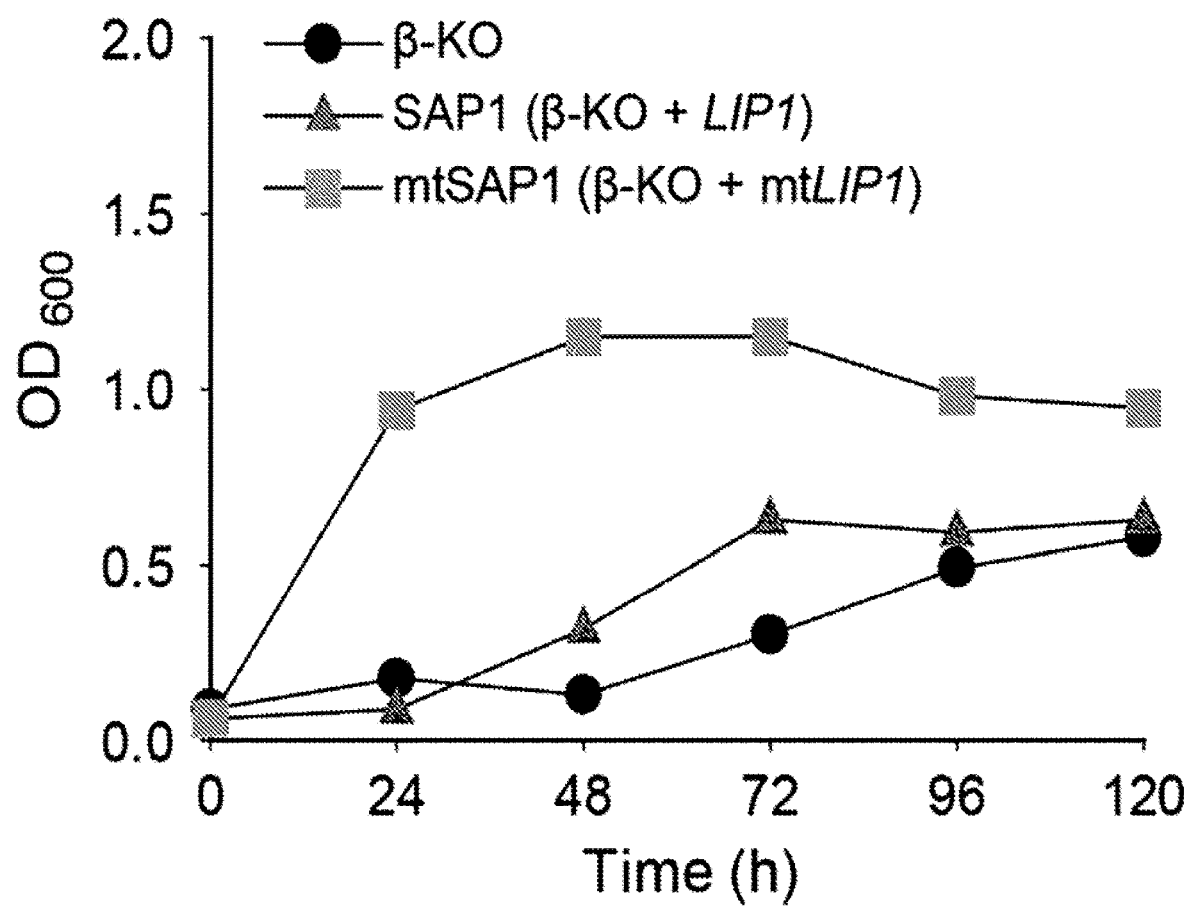

[Figure 7]
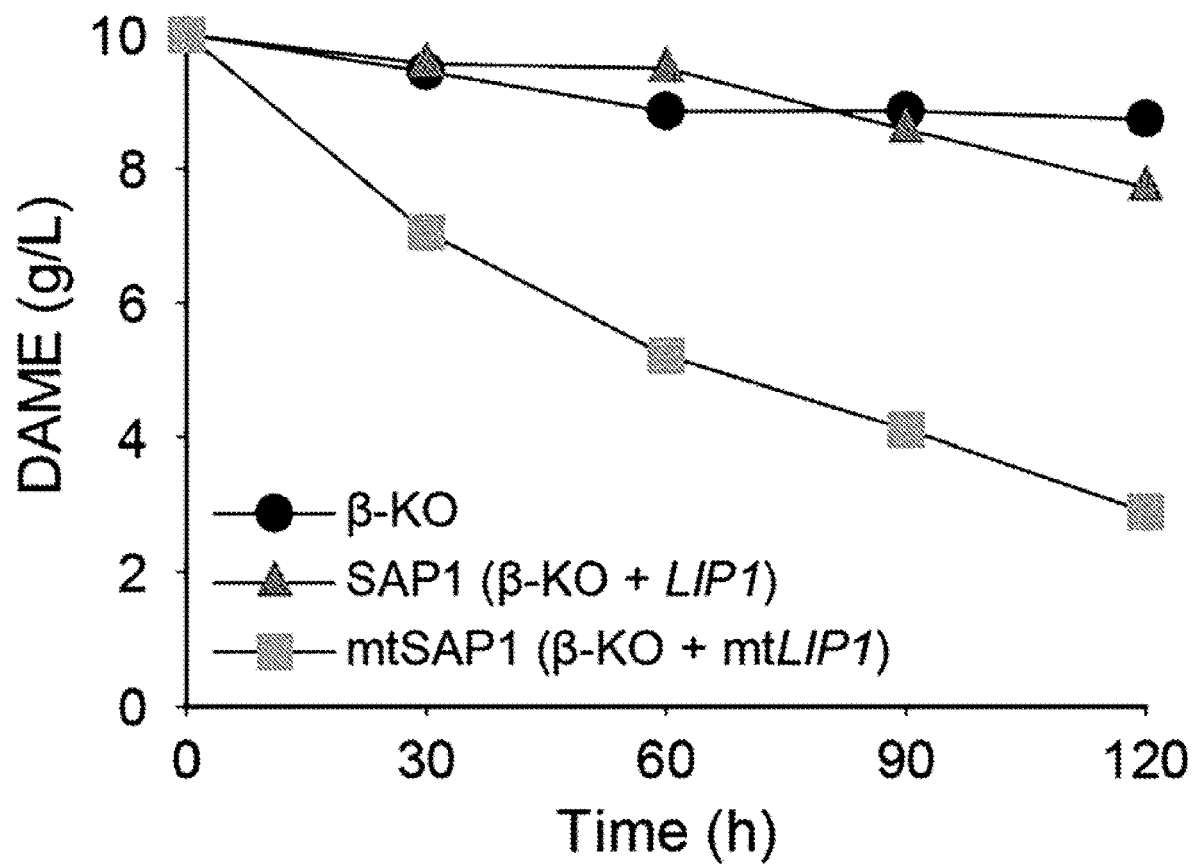

[Figure 8]
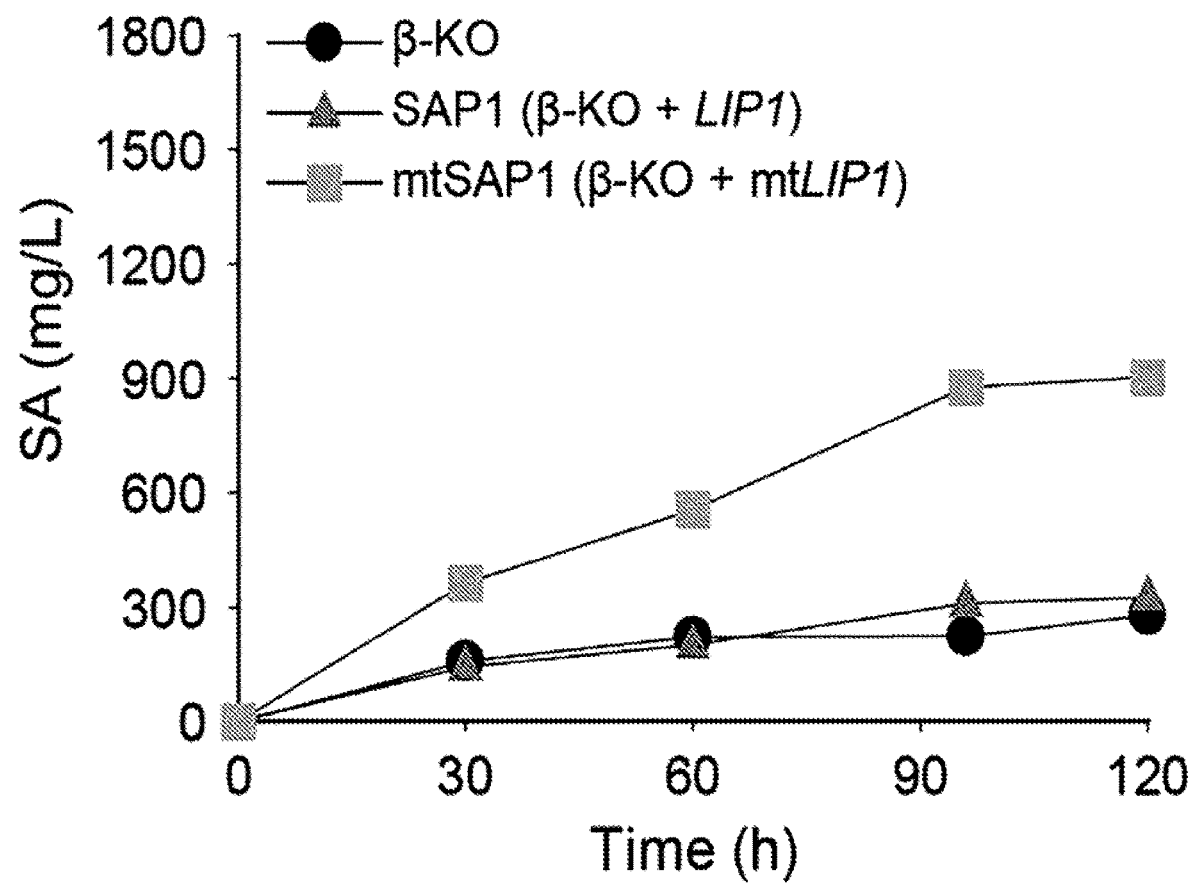

[Figure 9]
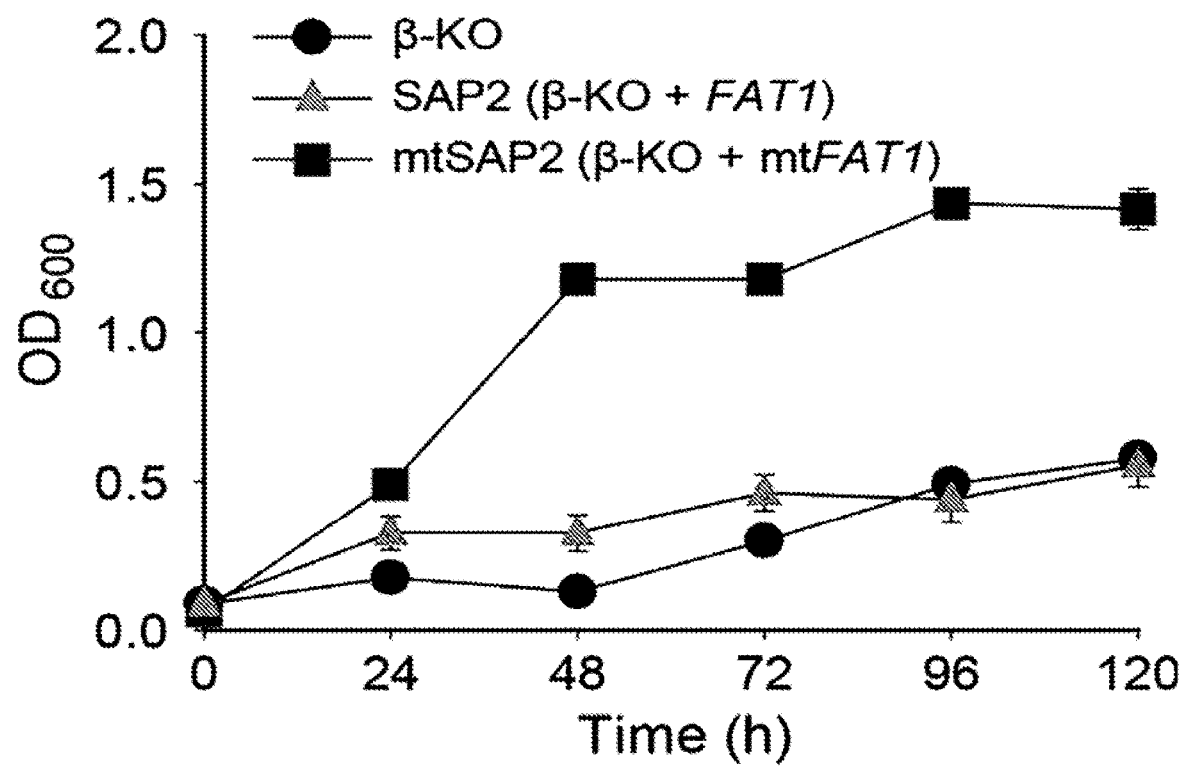

[Figure 10]
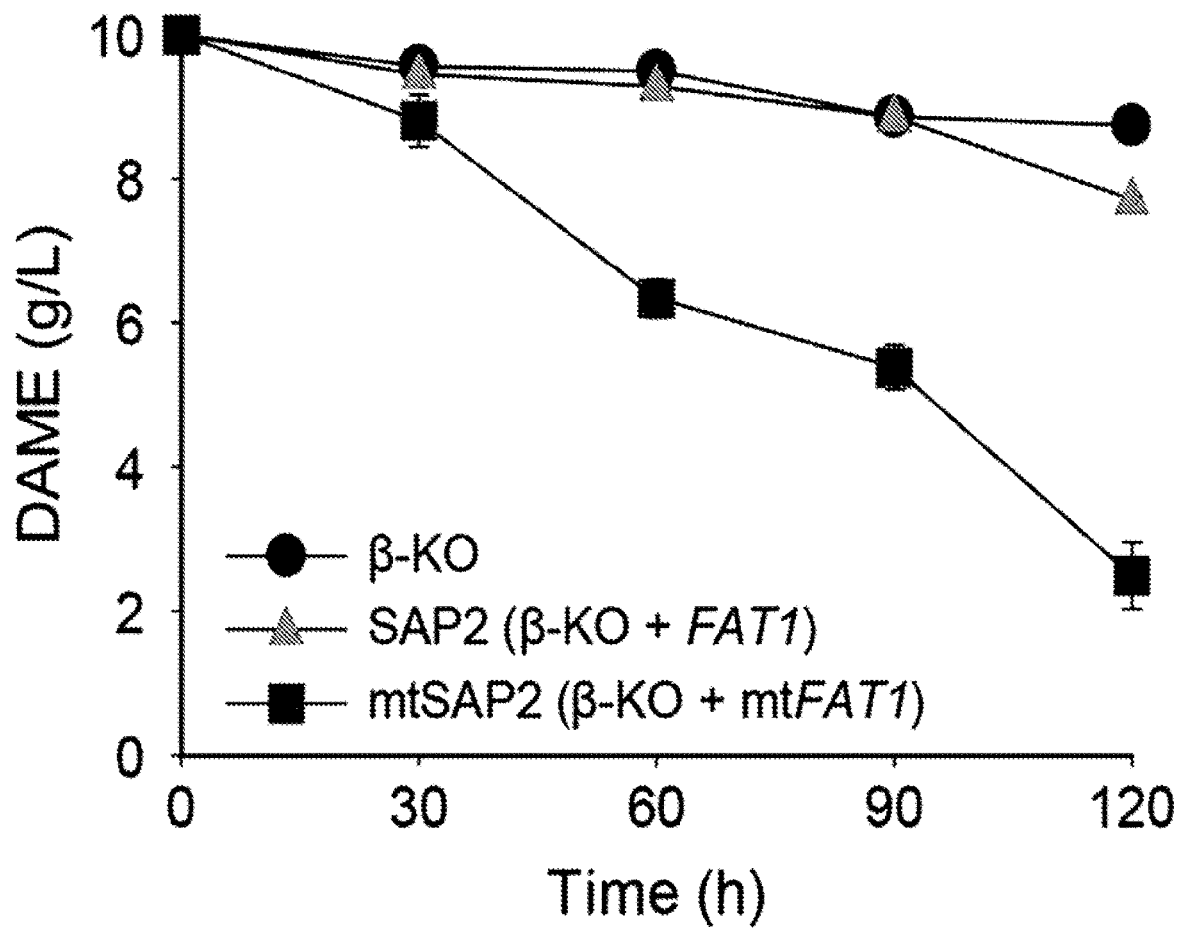

[Figure 11]
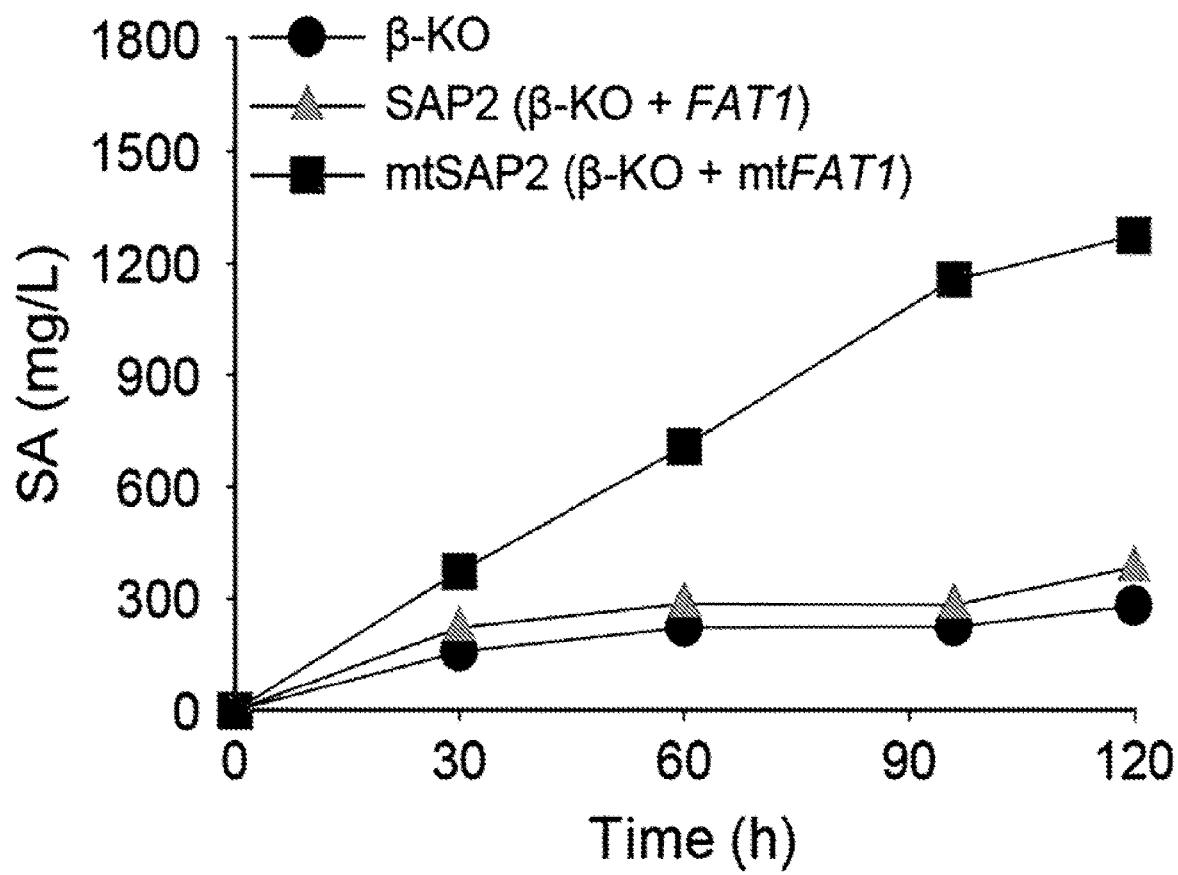

[Figure 12]
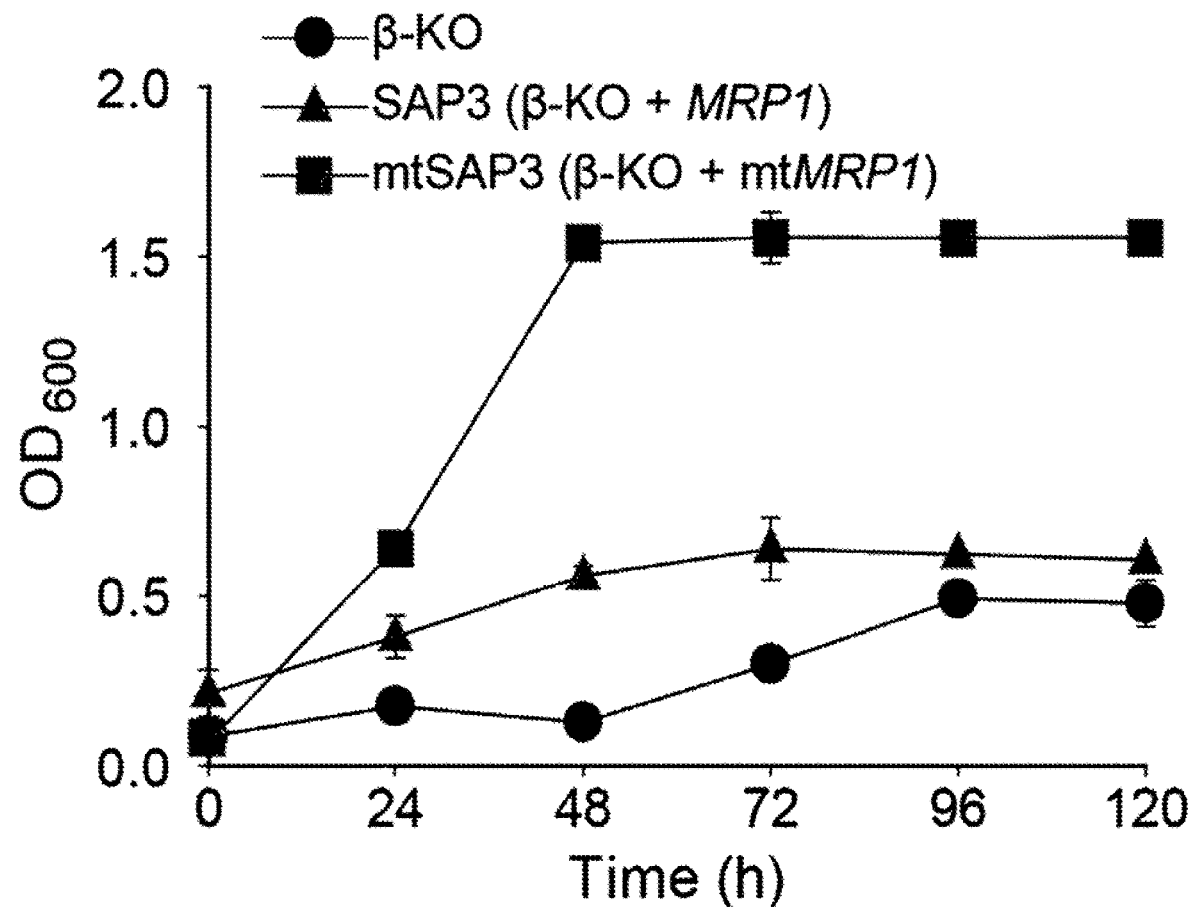

[Figure 13]
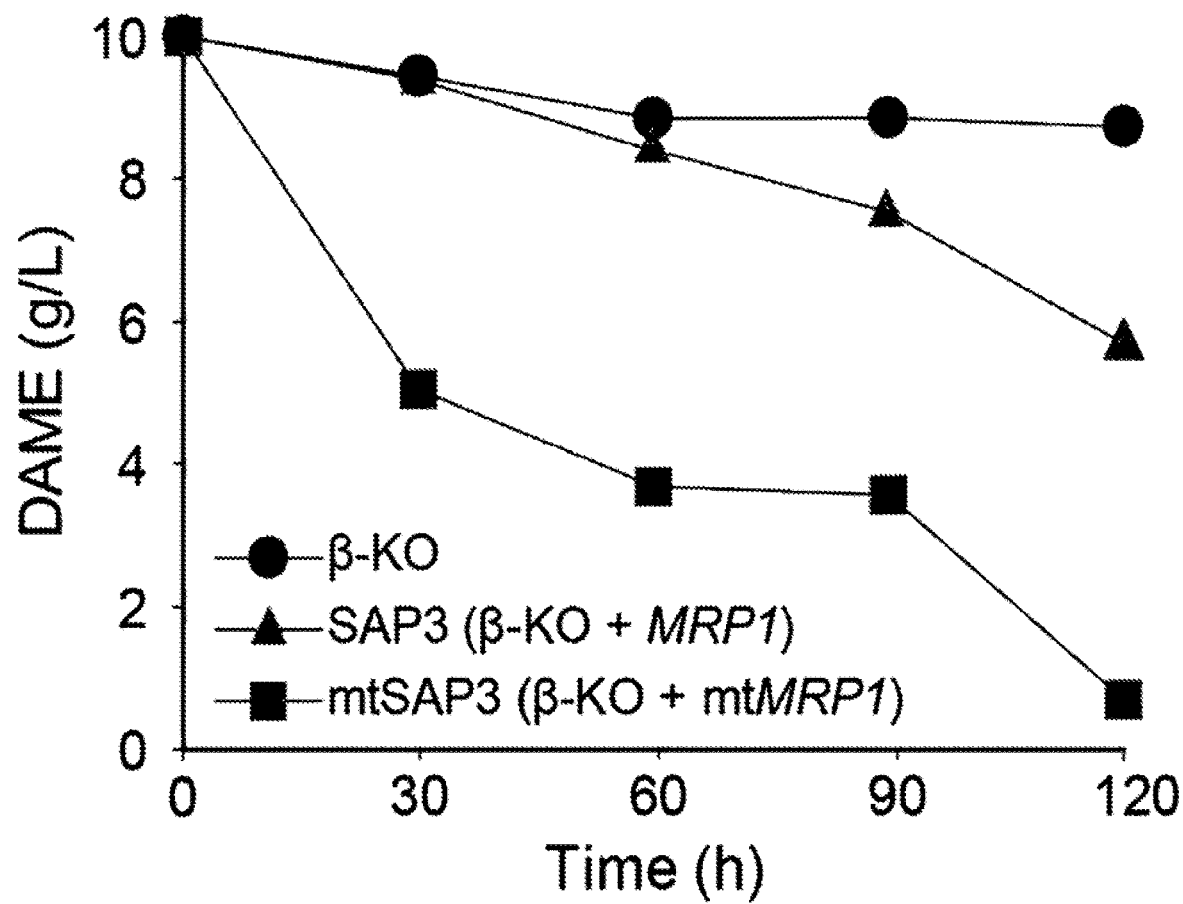

[Figure 14]
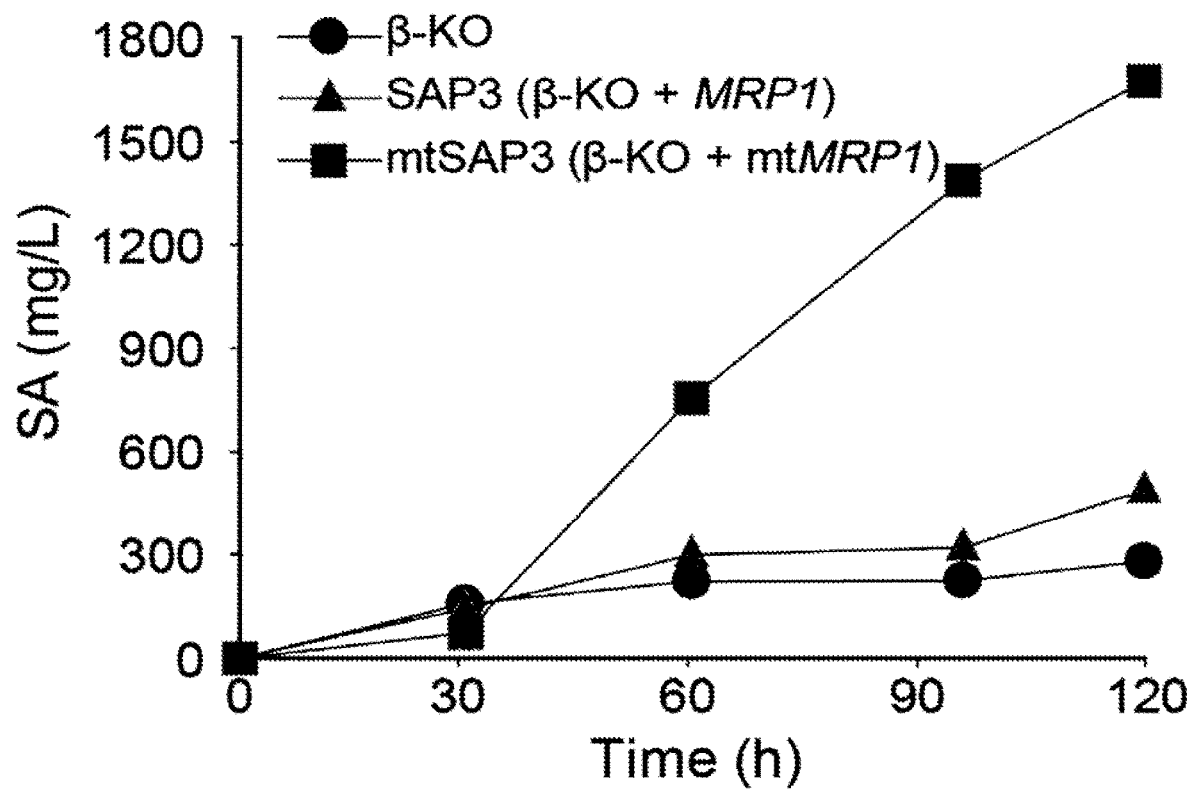

[Figure 15]
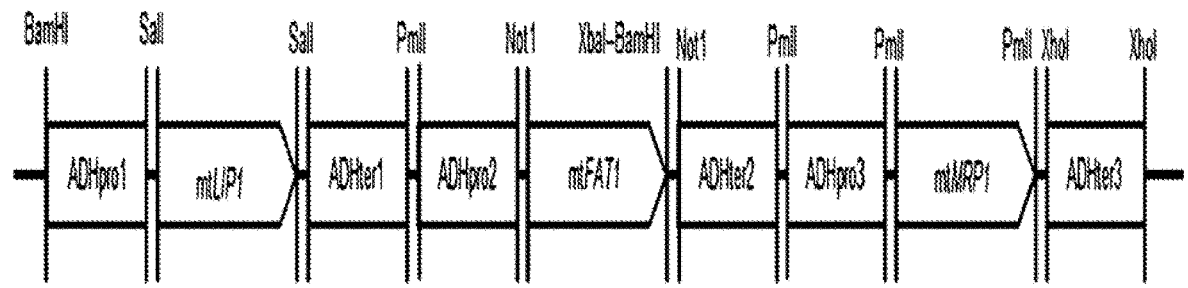
[Figure 16]
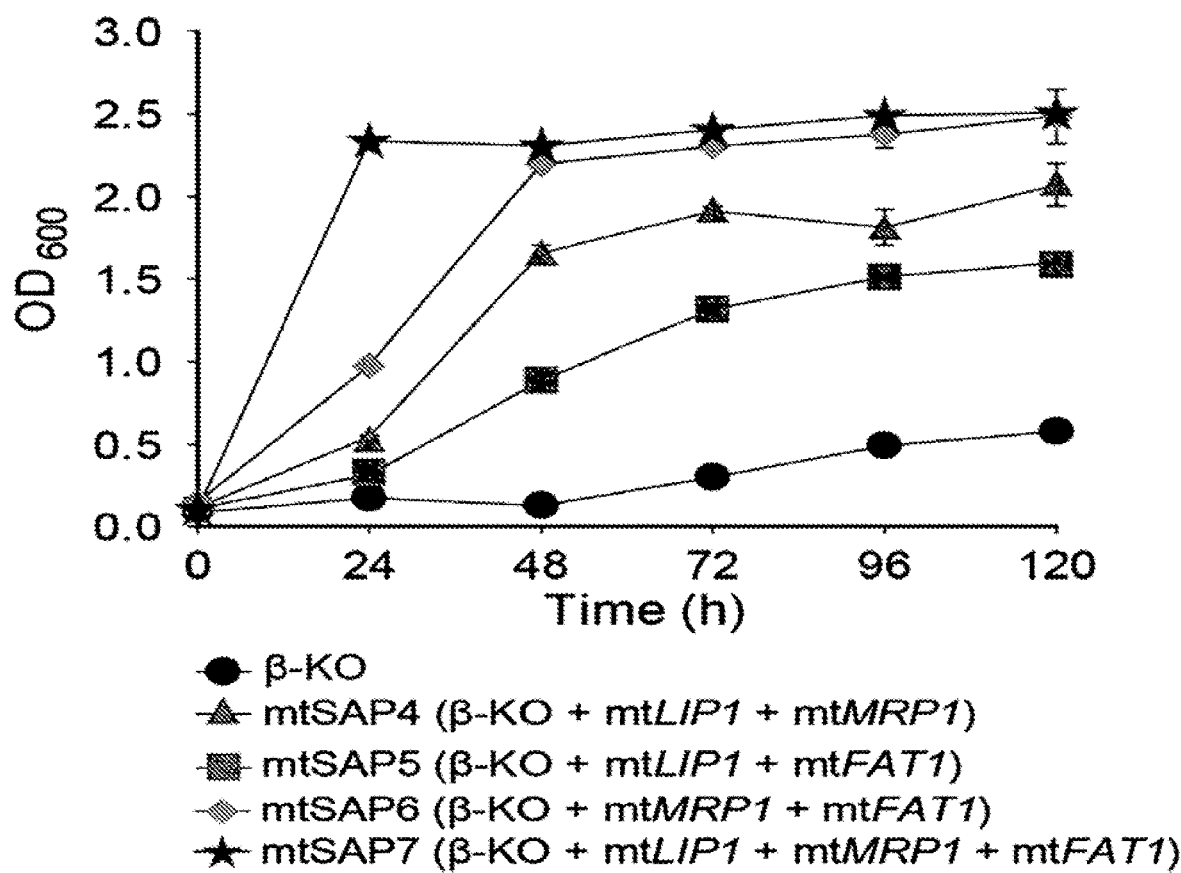

[Figure 17]
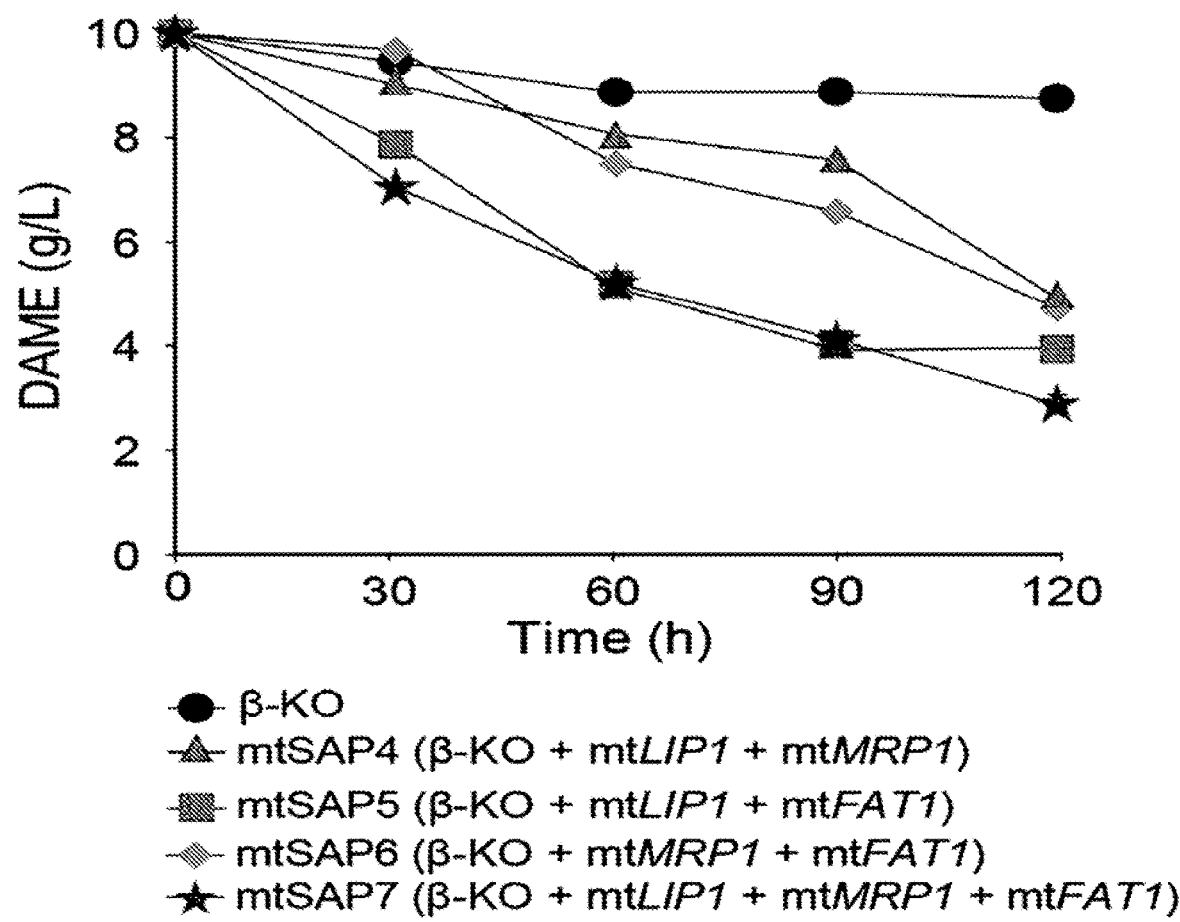

[Figure 18]
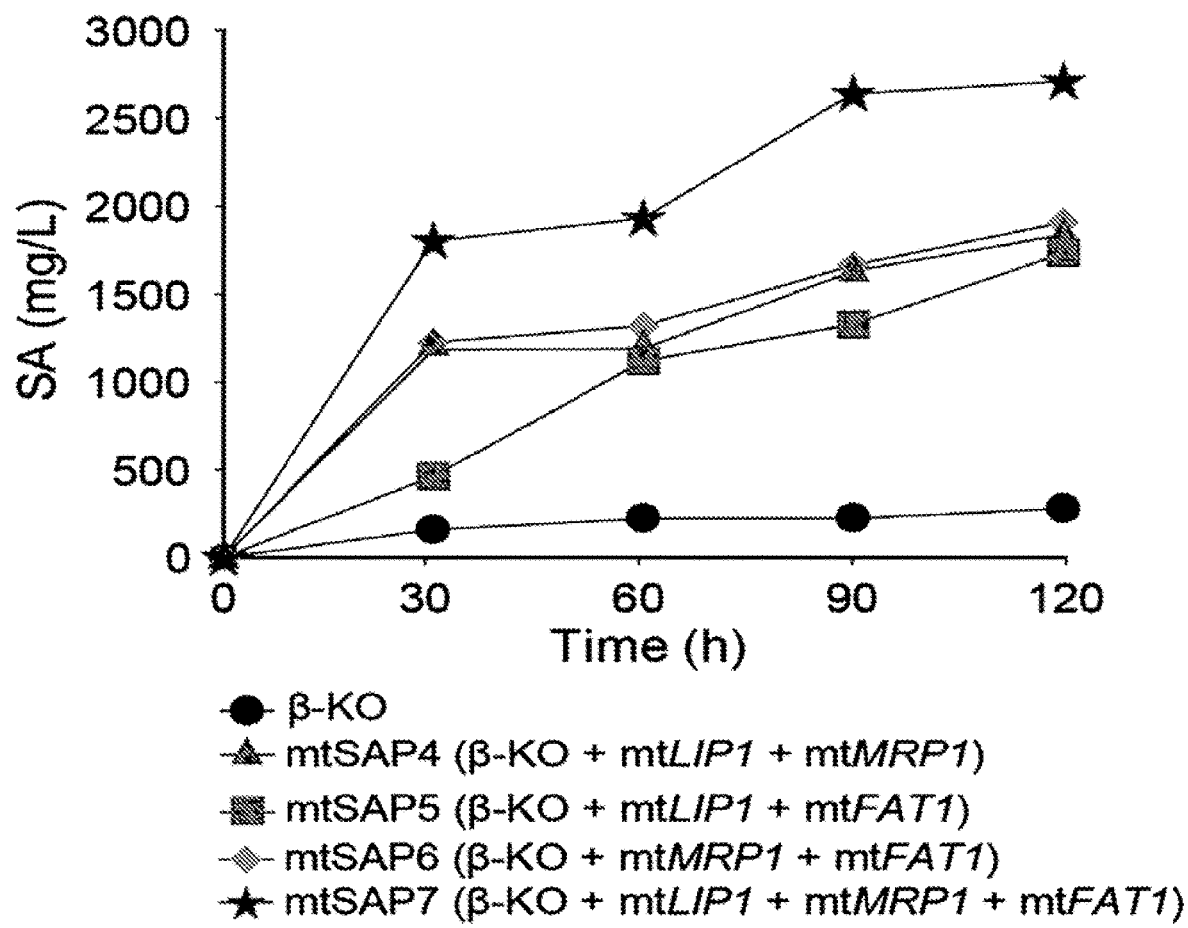

[Figure 19]
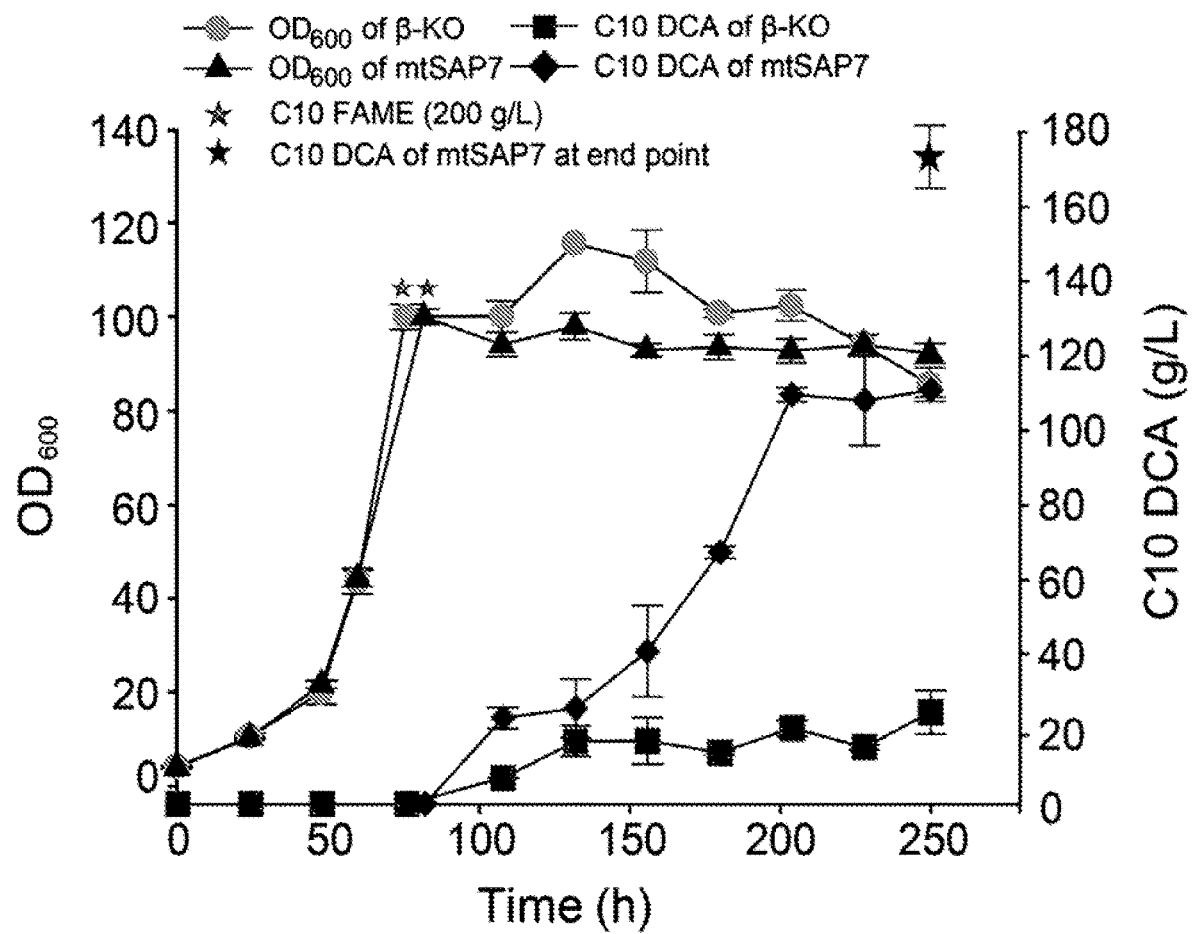

[Figure 20]
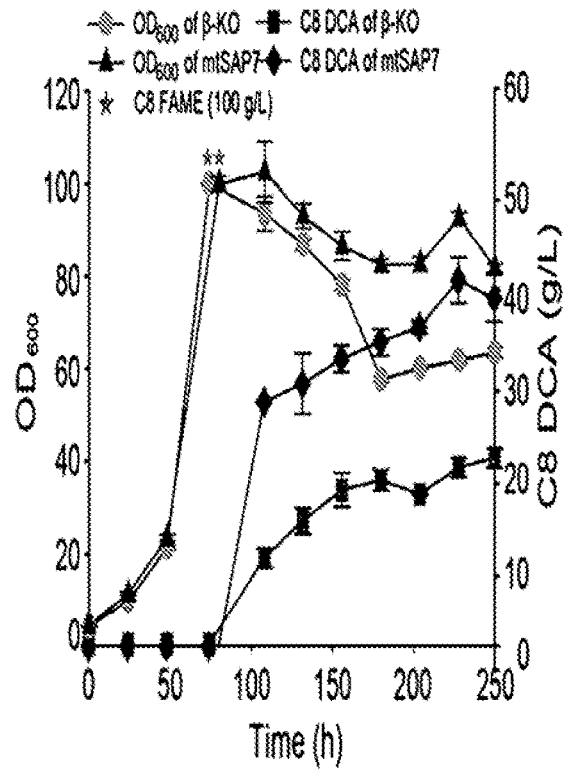
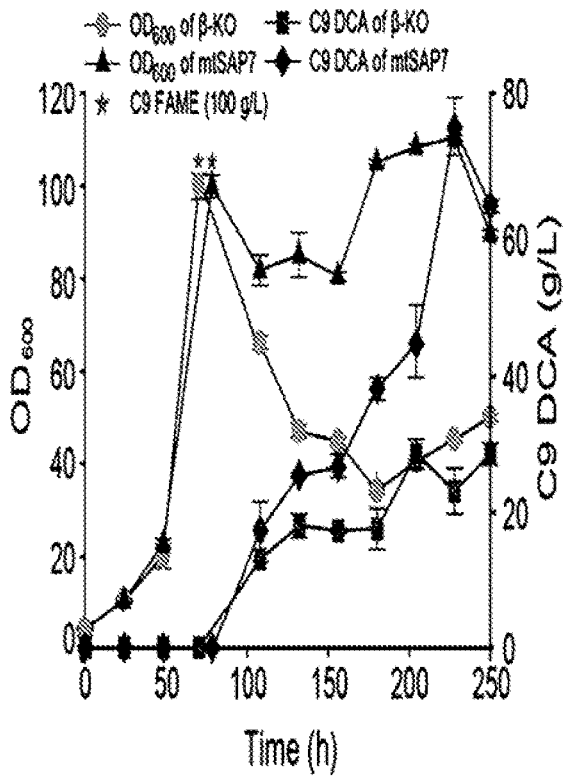
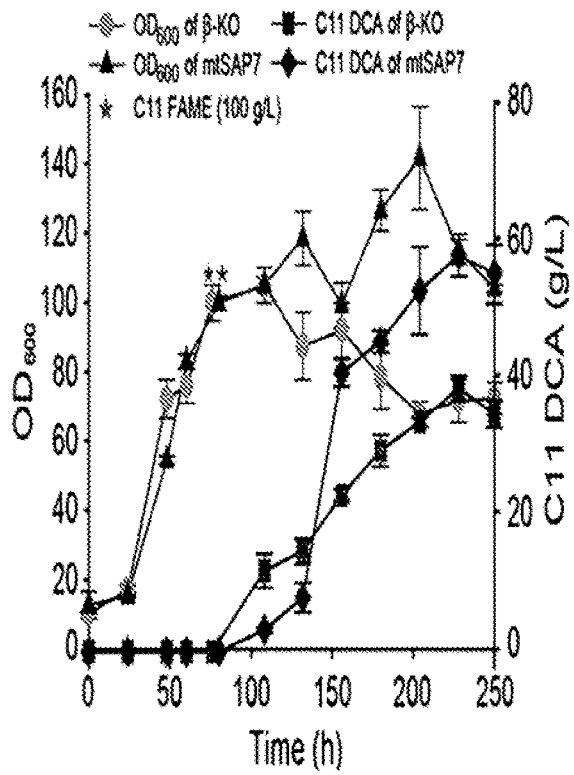
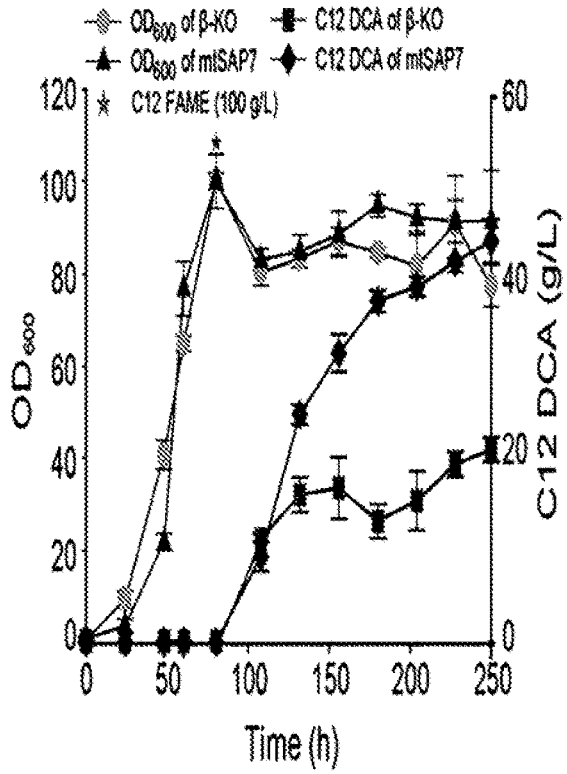

CANDIDA TROPICALIS STRAIN HAVING IMPROVED TOLERANCE TO THE CYTOTOXICITY OF SUBSTRATES, AND METHOD FOR PRODUCING DICARBOXYLIC ACID USING SAME

CROSS REFERENCE TO RELATED APPLICATIONS

This application is a National Stage of International Application No. PCT/KR2019/017044 filed Dec. 4, 2019, claiming priority based on Korean Patent Application No. 10-2018-0154372 filed Dec. 4, 2018, the entire disclosures of which are incorporated herein by reference.

TECHNICAL FIELD

The present invention relates to a microorganism having improved tolerance to the cytotoxicity of substrates, which includes a mutant gene, and method for producing a dicarboxylic acid (DCA) using the same.

BACKGROUND ART

Dicarboxylic acids (DCAs) are organic compounds containing two carboxyl groups (—COOH). The general molecular formula of dicarboxylic acids may be represented by $HO_2C-R-CO_2H$, wherein R may be an aliphatic or aromatic group. In general, dicarboxylic acids exhibit chemical reactions and reactivity similar to monocarboxylic acids. Dicarboxylic acids are also used to prepare copolymers such as polyamides and polyesters. The most widely used dicarboxylic acid in the industry is adipic acid, which is a precursor used in the production of nylon. Other examples of dicarboxylic acids include aspartic acid and glutamic acid, which are two amino acids in the human body. In addition, other carboxylic acids have been used in various industries fields.

Such dicarboxylic acids have been prepared by chemical processes or biological methods. As one example regarding the preparation of dicarboxylic acids, the synthesis of sebacic acid, which is one of the dicarboxylic acids, is possible even using phenol and cresol, but castor oil oxidation is known to be the most environmentally friendly and price-competitive method. Castor oil is transesterified by means of steam cracking, and ricinoleic acid is produced through the transesterification. When the ricinoleic acid thus produced is heated at 250° C. and then mixed with an alkali such as molten caustic soda, and the like, the ricinoleic acid is decomposed into capryl alcohol (2-octanol) and sebacic acid by means of caustic digestion. The product thus produced is purified to yield high-purity sebacic acid (U.S. Pat. Nos. 5,952,517 and 6,392,074). However, such a method has a drawback in that it requires a high-temperature process performed at 300° C. or higher to achieve the above, strong acids such as sulfuric acid are used, and large amounts of environmental contaminants are produced as substances such as heavy metals, toxic organic solvents, and the like are used therein. Such production is also possible by electrolyzing potassium monoethyl adipate in addition to using a chemical method for preparing sebacic acid.

In previous studies, it has been reported that dicarboxylic acids are biologically produced using a *Candida tropicalis* strain which has excellent ω-oxidation capacity and in which β-oxidation is blocked. However, this method has a limitation in that it does not effectively produce dicarboxylic acids because the *Candida tropicalis* strain has poor tolerance to substrates exhibiting cytotoxicity (Non-patent Document 1: David L. Craft, et al., Applied and Environmental Microbiology, 69 (10): 5983-5991, 2003). In particular, a Korean patent (Patent Application No. 10-2015-0149253) discloses that a mutant *Candida tropicalis* strain is used to produce sebacic acid from substrates having cytotoxicity, but there is no report on research of tolerance-enhancing factors and a sebacic acid-producing pathway. Therefore, it is important to develop a useful strain capable of mass-producing dicarboxylic acids using a biological method.

Accordingly, the present inventors have screened strains having improved tolerance to substrates having cytotoxicity to exhibit an enhanced ability to produce dicarboxylic acids by an evolutionary method using a *Candida tropicalis* strain producing dicarboxylic acids, and identified genes having an influence on the tolerance to the substrates from the *Candida tropicalis* strain. Therefore, the present invention has been completed on these facts.

Related-Art Document

Patent Document

Korean Patent Laid-Open Publication No. 10-2017-0048763

Non-Patent Document

David L. Craft, et al., Applied and Environmental Microbiology, 69 (10): 5983-5991, 2003

DISCLOSURE

Technical Problem

Therefore, it is an object of the present invention to provide a *Candida tropicalis* strain having improved tolerance to the cytotoxicity of substrates, wherein the strain comprise a mutation in one or more genes selected from a LIP1 (lipase) gene represented by a base sequence set forth in SEQ ID NO: 1, a FAT1 (fatty acid transport) gene represented by a base sequence set forth in SEQ ID NO: 2, and an MRP1 (multidrug resistance protein) gene represented by a base sequence set forth in SEQ ID NO: 3, or wherein the strain is transformed with one or more mutated genes selected from the mutated LIP1 gene, the mutated FAT1 gene and the mutated MRP1 gene.

It is another aspect of the present invention to provide a method for producing a dicarboxylic acid by incubating the *Candida tropicalis* strain with a substrate.

Technical Solution

To achieve the above objects, the present invention provides A *Candida tropicalis* strain having improved tolerance to the cytotoxicity of substrates, wherein the strain comprise a mutation in one or more genes selected from a LIP1 (lipase) gene represented by a base sequence set forth in SEQ ID NO: 1, a FAT1 (fatty acid transport) gene represented by a base sequence set forth in SEQ ID NO: 2, and an MRP1 (multidrug resistance protein) gene represented by a base sequence set forth in SEQ ID NO: 3, or wherein the strain is transformed with one or more mutated genes selected from the mutated LIP1 gene, the mutated FAT1 gene and the mutated MRP1 gene.

According to one embodiment, when normal *Candida tropicalis* strains are incubated in a medium containing a substrate exhibiting cytotoxicity to screen the strains having an excellent ability to survive in the substrate in an evolutionary aspect, it has been found through the genome analysis of the screened strains that one or more endogenous genes selected from a LIP1 (lipase) gene represented by a base sequence set forth in SEQ ID NO: 1, a FAT1 (fatty acid transport) gene represented by a base sequence set forth in SEQ ID NO: 2, and an MRP1 (multidrug resistance protein) gene represented by a base sequence set forth in SEQ ID NO: 3 are mutated. Also, it has been found that, when the mutated gene is isolated and separately transduced into the normal Candida tropicalis strain, the Candida tropicalis strain has improved tolerance to the substrates exhibiting cytotoxicity.

A base sequence of the mutated mtLIP1 (lipase) gene of the LIP1 (lipase) gene represented by a base sequence set forth in SEQ ID NO: 1 may be set forth in SEQ ID NO: 4, a base sequence of the mutated mtFAT1 (fatty acid transport) gene of the FAT1 (fatty acid transport) gene represented by a base sequence set forth in SEQ ID NO: 2 may be set forth in SEQ ID NO: 5, or a base sequence of the mutated mtMRP1 (multidrug resistance protein) gene of the MRP1 (multidrug resistance protein) gene represented by a base sequence set forth in SEQ ID NO: 3 may be set forth in SEQ ID NO: 6.

One or more of the mutated genes may be included in a vector. The vector may be in a form in which genes can be operably linked. In the present invention, the term "operably linked" generally means that a base-expressing regulatory sequence is operably linked to a base sequence encoding a desired protein to perform its function, thereby exerting an influence on the expression of the base sequence encoding the desired protein. The operable linking of the vector may be achieved using genetic recombination techniques known in the art, and site-specific DNA digestion and ligation may be performed using digestion and ligation enzymes and the like known in the art.

In the present invention, the term "vector" refers to any medium for cloning and/or transferring bases into a host cell. The vector may be a replicon that may bind to another DNA fragment to replicate the bound fragment. The term "replicon" refers to any genetic unit (for example, a plasmid, a phage, a cosmid, a chromosome, a virus) that functions in vivo as an autologous unit of DNA replication, that is, is replicable through its own regulation. The term "vector" may include viral and non-viral mediums for introducing bases into a host cell in vitro, ex vivo, or in vivo. Also, the term "vector" may include mini-spherical DNA. For example, the vector may be a plasmid that does not have a bacterial DNA sequence. The term "vector" may also include a transposon such as Sleeping Beauty (Izsvak et. al. J. Mol. Biol. 302:93-102 (2000)), or an artificial chromosome. Examples of commonly used vectors include naturally occurring or recombinant plasmids, cosmids, viruses, and bacteriophages. For example, pWE15, M13, MBL3, MBL4, IXII, ASHII, APII, t10, t11, Charon4A, Charon21A, and the like may be used as the phage vector or the cosmid vector. A plasmid vector may also be used. Vectors that may be used in the present invention are not particularly limited, and known expression vectors may be used.

The Candida tropicalis strain may express the mutated genes, or may include a vector containing the mutated genes.

The Candida tropicalis strain is a strain whose β-oxidation pathway is blocked. Particularly, the Candida tropicalis strain may be a strain whose β-oxidation pathway is blocked, thereby producing dicarboxylic acids using a substrate.

The substrate may be a fatty acid methyl ester (FAME). In this case, the substrate exhibits cytotoxicity toward the Candida tropicalis strain producing the dicarboxylic acids. Particularly, the fatty acid methyl ester may be one of fatty acid methyl esters including a $C_6$-$C_{20}$ alkylene group. More particularly, the fatty acid methyl ester may be decanoic acid methyl ester (DAME).

According to one embodiment of the present invention, it is confirmed that the Candida tropicalis strain in which one or more genes selected from a LIP1 (lipase) gene represented by a base sequence set forth in SEQ ID NO: 1, a FAT1 (fatty acid transport) gene represented by a base sequence set forth in SEQ ID NO: 2, and an MRP1 (multidrug resistance protein) gene represented by a base sequence set forth in SEQ ID NO: 3 are mutated, or the Candida tropicalis strain into which one or more of the mutated genes are introduced has improved tolerance to the cytotoxicity of the fatty acid methyl ester, thereby exhibiting an excellent ability to survive in the substrates.

According to another aspect, the present invention provides a method for producing a dicarboxylic acid (DCA), which includes incubating, with a substrate, the Candida tropicalis strain having improved tolerance to the cytotoxicity of substrates, in which one or more genes selected from a LIP1 (lipase) gene represented by a base sequence set forth in SEQ ID NO: 1, a FAT1 (fatty acid transport) gene represented by a base sequence set forth in SEQ ID NO: 2, and an MRP1 (multidrug resistance protein) gene represented by a base sequence set forth in SEQ ID NO: 3 are mutated, or into which one or more of the mutated genes are introduced.

Because the method for producing a dicarboxylic acid according to the present invention uses the above-described Candida tropicalis strain as it is, description of the common contents between the two is omitted to avoid excessive complexity of this specification.

The Candida tropicalis strain may be a strain whose β-oxidation pathway is blocked.

The substrate required for dicarboxylic acid production of the Candida tropicalis strain may be a fatty acid methyl ester (FAME). In this case, the substrate exhibits cytotoxicity to the Candida tropicalis strain producing dicarboxylic acids. Particularly, the fatty acid methyl ester may be one of fatty acid methyl esters having a $C_6$-$C_{20}$ alkyl chain.

According to one embodiment of the present invention, a mutant strain, which is obtained by introducing one or more genes selected from the mutated mtLIP1 (lipase) gene of the LIP1 (lipase) gene represented by a base sequence set forth in SEQ ID NO: 1, the mutated mtFAT1 (fatty acid transport) gene of the FAT1 (fatty acid transport) gene represented by a base sequence set forth in SEQ ID NO: 2, and the mutated mtMRP1 (multidrug resistance protein) gene of the MRP1 (multidrug resistance protein) gene represented by a base sequence set forth in SEQ ID NO: 3 into the Candida tropicalis strain whose β-oxidation pathway is blocked, is prepared, and used in an experiment for producing dicarboxylic acids. The dicarboxylic acid production abilities of the mutant Candida tropicalis strain and the Candida tropicalis strain whose β oxidation pathway is blocked are compared. As a result, it is confirmed that the mutant Candida tropicalis strain of the present invention has a superior ability to produce dicarboxylic acids, which indicates that the tolerance of the Candida tropicalis strain to the cytotoxicity of the substrates is improved through the mutation of the disclosed genes, which results in improved viability of the strain.

Advantageous Effects

The *Candida tropicalis* strain for producing dicarboxylic acids developed according to the present invention has improved tolerance to existing toxic substrates as well as significantly improved dicarboxylic acid production efficiency compared to existing strains, and thus is expected to have high industrial utility because the *Candida tropicalis* strain is applicable to a biological process for producing dicarboxylic acids.

DESCRIPTION OF DRAWINGS

FIG. 1 shows the results of comparing the cytotoxicities of decanoic acid methyl ester (DAME), decanoic acid (DA) and sebacic acid (SA) to a *Candida tropicalis* strain.

FIG. 2 shows a growth graph of mutant *Candida tropicalis* strains according to generation time: E1 (170 generation time), E2 (470 generation time), E4 (700 generation time), E5 (720 generation time), and ES5.

FIG. 3 shows the results of measuring a dry cell weight (DCW) of each of the mutant *Candida tropicalis* strains (WT, E5, and ES5).

FIG. 4 shows the results of analyzing an amount of DAME consumption in a medium of each of the mutant *Candida tropicalis* strains (WT, E5, and ES5).

FIG. 5 shows the results of analyzing an amount of sebacic acid production by each of the mutant *Candida tropicalis* strains (WT, E5, and ES5).

FIGS. 6 to 8 show the results of comparing and analyzing the dry cell weights (FIG. 6), the amounts of DAME consumption (FIG. 7), and the amounts of sebacic acid production (FIG. 8) of the mutant *Candida tropicalis* strain (mtSAP1) into which an mtLIP1 gene is introduced, the strain (β-KO) from which a β-oxidation pathway is deleted as a parent strain, and the strain (SAP1) into which a LIP1 gene is introduced.

FIGS. 9 to 11 show the results of comparing and analyzing the dry cell weights (FIG. 9), the amounts of DAME consumption (FIG. 10), and the amounts of sebacic acid production (FIG. 11) of the mutant *Candida tropicalis* strain (mtSAP2) into which an mtFAT1 gene is introduced, the strain (β-KO) from which a β-oxidation pathway is deleted as a parent strain, and the strain (SAP2) into which a FAT1 gene is introduced.

FIGS. 12 to 14 show the results of comparing and analyzing the dry cell weights (FIG. 12), the amounts of DAME consumption (FIG. 13), and the amounts of sebacic acid production (FIG. 14) of the mutant *Candida tropicalis* strain (mtSAP3) into which an mtMRP1 gene is introduced, the strain (β-KO) from which a β-oxidation pathway is deleted as a parent strain, and the strain (SAP3) into which an MRP1 gene is introduced.

FIG. 15 is a schematic diagram of a plasmid vector for transducing *Candida tropicalis*, which includes an mtLIP1 gene, an mtFAT1 gene, and an mtMRP1 gene.

FIGS. 16 to 18 show the results of analyzing a dry cell weight (FIG. 16), an amount of DAME consumption (FIG. 17) and an amount of sebacic acid production (FIG. 18) of the mutant *Candida tropicalis* strain into which two or more genes of the mtLIP1 gene, the mtFAT1 gene, and the mtMRP1 gene are introduced.

FIG. 19 shows the results of confirming the cytotoxicity tolerance of the mutant *Candida tropicalis* strain (mtSAP7), into which the mtLIP1 gene, the mtFAT1 gene, and the mtMRP1 gene are introduced, and the parent strain (β-KO) to the $C_{10}$ fatty acid methyl ester (FAME) substrate by measuring the dry cell weights and the amount of dicarboxylic acid production of the mutant *Candida tropicalis* strain (mtSAP7) and the parent strain (β-KO).

FIG. 20 shows the results of confirming the cytotoxicity tolerance of the mutant *Candida tropicalis* strain (mtSAP7), into which the mtLIP1 gene, the mtFAT1 gene, and the mtMRP1 gene are introduced, and the parent strain (β-KO) to the $C_8$ to $C_{12}$ fatty acid methyl ester (FAME) substrate by measuring the dry cell weights and the amount of dicarboxylic acid production of the mutant *Candida tropicalis* strain (mtSAP7) and the parent strain (3-KO).

BEST MODE

Hereinafter, the constitution and the effects of the present invention will be described in further detail with reference to embodiments thereof. However, it should be understood that the embodiments described herein are merely provided for exemplary illustration of the present invention, and are not intended to limit the scope of the present invention.

[Example 1] Confirmation of Biological Cytotoxicity of Substrates and Products

To confirm the cytotoxicity of decanoic acid methyl ester (DAME) used as a substrate for production of sebacic acid, and a product thereof (i.e., sebacic acid), a toxicity test was performed under the following conditions. More particularly, a *Candida tropicalis* MYA_3404 strain, which had been used in the related art to produce sebacic acid, was incubated in a YNB medium (10 g/L of a yeast extract, and 20 g/L of peptone) to which DAME, DA, or sebacic acid was added at a concentration of 5 g/L. The incubation temperature was 30° C., and the strain was incubated at 200 rpm for 36 hours.

As a result, as shown in FIG. 1, it was confirmed that the strain grew at a slower growth rate or did not grow in the medium to which DAME, DA, or sebacic acid were added, compared to the control to which none of DAME, DA, and sebacic acid were added. More particularly, it was confirmed that the growth rate and the total cell mass of the strain decreased in the medium to which sebacic acid was added, compared to the control, and it was confirmed that the strain did not grow in the medium to which DAME or DA was added at a concentration of 5 g/L. Based on the results, it was confirmed that all the substrates (DAME and DA) and the product (sebacic acid) had cytotoxicity. Among these, it was confirmed that DAME had stronger cytotoxicity, compared to the sebacic acid. From the above-described results, it was confirmed that there was a preferential need for development of a strain having tolerance to DAME as the substrate in order to produce a high concentration of sebacic acid.

[Example 2] Development of DAME-Tolerant Strain Using Evolutionary Engineering Method To develop a strain having tolerance to DAME, which is a substrate having cytotoxicity, a *C. tropicalis* MYA_3404 strain was incubated in a YNB medium (10 g/L of a yeast extract and 20 g/L of peptone) to which DAME was added at a concentration of 10 g/L. In this case, it was confirmed that a concentration of DAME in the medium was maintained to be approximately 0.45 g/L (maximal solubility) due to the low solubility of the DAME substrate (confirmed through the results of internal experiments). The growth curve of the inoculated strain was determined by measuring an absorbance value at a wavelength of 600 nm.

The absorbance of the medium in which the strain was inoculated was observed in real time, and the strain was then sub-cultured in a fresh medium until the growth of the strain reached a mid-exponential phase. A specific growth rate was calculated from the measured absorbance value, and the strains having phases where a specific growth rate changed greatly were determined to be E1 (170 generation time), E2 (470 generation time), E4 (700 generation time), and E5 (720 generation time), respectively. Also, the E5 strain obtained by the method as described above was sub-cultured in a YNB medium (10 g/L of a yeast extract and 20 g/L of peptone) supplemented with 20 g/L of glucose as a non-toxic carbon source, and then re-incubated in a DAME substrate to screen a strain whose tolerance to DAME was maintained even after replacing the carbon source, which was named "ES5."

The growth profiles of the mutant strains were determined. As a result, it was confirmed that the specific growth rates of the mutant strains increased as the subculture proceeded as shown in FIG. 2. It was confirmed that the ES5 strain also exhibited a high specific growth rate without losing its tolerance, and had a constant tolerance to the DAME substrate. To more specifically determine the specific growth rate and the tolerance to the DAME substrate, the WT strain as the control and the E5 and ES5 strains as the mutant strains were incubated in a YNB medium to which DAME was added at a concentration of 10 g/L. The incubation temperature was 30° C., the incubation period was 120 hours, and samples were collected every 12 hours or 24 hours to measure the dry cell weights (DCWs) of the samples.

The dry cell weight (DCW) of each of the strains was measured. As a result, as shown in FIG. 3, it was confirmed that the WT strain had a very low DCW value (did not grow), whereas the E5 and ES5 strains had maximum cell masses after 120 hours of incubation of the strains, and the cell masses of the ES5 and E5 strains increased to 2.5 g/L and 2.2 g/L, respectively. Based on the results, it was confirmed that the mutant strains E5 and ES5 obtained by the evolutionary engineering method had tolerance to the DAME substrate, and thus grew to a greater extent.

[Example 3] Confirmation of Phenotypic Changes of Parent Strain (WT) and Mutant Strains (E5 and ES5)

The actual amounts of DAME substrate consumption and amounts of sebacic acid production of the mutant strains E5 and ES5 obtained in Example 2 were compared to those of the parent strain (WT). To determine the DAME substrate consumption and the sebacic acid productivity, each of the WT, E5, and ES5 strains was incubated in a YNB medium to which DAME was added at a concentration of 10 g/L at a temperature of 30° C. for 120 hours.

The samples for analysis were collected every 12 hours or 24 hours to analyze concentrations of DAME and sebacic acid in the medium using gas chromatography/mass spectrometry (GC/MS). The GC/MS conditions are as listed in the following Table 1.

TABLE 1

| Parameters | Conditions |
| --- | --- |
| Carrier gas | Helium |
| Oven temperature | 100° C. for 3.5 min |
|  | 80-160° C. at 15° C., ° C./min held for 20 min |
|  | 160-200° C. at 15° C., ° C./min held for 15 min |
|  | 200-280° C. at 15° C., ° C./min held for 5 min |
| Injector temperature | 250° C. |
| Split ratio | 01:09.6 |
| Injection volume | 1 μL |
| Electronic impact | 70 eV |
| Scan range | 50-600, m/z |
| Interface temperature | 280° C. |
| Column | DB-5MS capillary column |
|  | (30 m × 25 mm, 0.25 μm film thickness) |
| Ion source temperature | 230° C. |

The sample for GC/MS analysis used to analyze DAME was prepared as follows. 4 mL of the collected culture solution was mixed with 1 mL of 10 M HCL, and vortexed for one minute. An equivalent amount of hexane was added to the mixture, and incubated at room temperature for 10 minutes. After 10 minutes, the mixture was thoroughly mixed by vortexing, and then centrifuged at 12,000 rpm for 1 minute. A supernatant (hexane) was collected from the mixed solution in which two layers are separated, and used for GC/MS analysis. Like the previous DAME analysis of the collected sample, 10 M HCL was added to a sample for analysis of sebacic acid, and then mixed. Thereafter, an equivalent amount of ethyl acetate was added thereto, and mixed. Then, an ethyl acetate layer was collected, and completely dried using a vacuum evaporator. Subsequently, 50 μL of pyridine (Sigma-Aldrich, St Louis, MO, USA) was added to a 2% (w/v) concentration of O-methylhydroxylamine hydrochloride (Sigma-Aldrich, St Louis, MO, USA), and then subjected to methoximation at 75° C. for 30 minutes. Then, 80 μL of N-methyl-N-(trimethylsilyl) trifluoroacetamide (Sigma-Aldrich, St Louis, MO, USA) was added thereto, and then subjected to derivatization at 40° C. for 30 minutes. To quantify the analysis results, DAME and sebacic acid were purchased (Sigma-Aldrich, St Louis, MO, USA), and diluted at a certain ratio. Then, a sample for analysis was prepared in the same manner as described above, and then analyzed by GC/MS. The collected sample was analyzed by GC/MS to measure an amount of DAME of the medium. As a result, as shown in FIG. 4, it was confirmed that the amount of DAME did not greatly decrease in the medium in which the parent strain was inoculated, whereas the amount of substrate rapidly decreased in the media in which the E5 strain and the ES5 strain were inoculated. Therefore, it was confirmed that, after the elapse of 120 hours at which the strain reached the maximum cell mass, DAME was present at approximately 3.1 g/L in the medium in which the E5 strain was inoculated, and DAME was present at approximately 2.8 g/L in the medium in which the ES5 strain was inoculated. Also, the amounts of sebacic acid production (FIG. 5) of the E5 and ES5 strains were greatly different from that of the parent strain. In this case, it was confirmed that the amount of sebacic acid production of the parent strain was approximately 44.3 mg/L after 48 hours of fermentation, whereas the amounts of sebacic acid production of the E5 strain and the ES5 strain were shown to be approximately 177.4 g/L and approximately 218.4 mg/L, respectively. As such, the fact that the E5 and ES5 strains exhibit high DAME substrate consumption and sebacic acid productivity is judged to be due to the mutations in the strains when the strains were sub-cultured with DAME which is a substrate having biological toxicity. Therefore, base sequencing and transcriptome analysis were performed on the ES5 strain exhibiting the highest DAME consumption and sebacic acid productivity.

[Example 4] Transcriptome Analysis of DAME-Tolerant Mutant Strain (ES5)

To check a change of a transcriptome in media with and without DAME, the transcriptomes of an ES5 strain grown in a medium supplemented with DAME and an ES5 strain grown in a DAME-free medium were analyzed.

The ES5 strains were incubated in a DAME-free YNB medium and a YNB medium supplemented with 10 g/L of DAME at 30° C. for 24 hours. The incubated cells were collected, and washed with water. Thereafter, the collected cells were used as a sample for whole RNA extraction. The RNA extraction was performed using an RNeasy Mini Kit (Qiagen, Hilden, Germany), and the concentration and purity of the extracted RNA were measured using NanoDrop (Thermo Scientific, Wilmington, DE, USA) and Agilent Bioanalyzer 2100 (Santa Clara, Ca, USA), respectively.

The transcriptome of the mutant ES5 strain was analyzed, and compared with that of the parent strain. As a result, it was confirmed that a total of 453 genes were upregulated in the ES5 strain, compared to the parent strain, and 147 genes were downregulated in the ES5 strain, compared to the parent strain. The details of the number and clusters of the genes are specified in Table 2.

TABLE 2

Results of comparison/analysis of transcriptomes of parent strain and DAME-tolerant mutant strain (ES5)

| No | Pathway | No of Upregulated Genes | No of Downregulated Genes |
|---|---|---|---|
| 1 | Alanine, aspartate, and glutamate metabolisms | 12 | |
| 2 | alpha-Linolenic acid metabolism | 9 | |
| 3 | Arginine and proline metabolisms | 12 | |
| 4 | Arginine biosynthesis | 9 | |
| 5 | Ascorbate and aldarate metabolisms | 6 | |
| 6 | Beta-Alanine metabolism | 15 | 6 |
| 7 | Biosynthesis of antibiotics | 51 | |
| 8 | Biosynthesis of unsaturated fatty acids | 12 | |
| 9 | Biotin metabolism | 6 | |
| 10 | Butanoate metabolism | 9 | 6 |
| 11 | Cell cycle - yeast | | 12 |
| 12 | Cysteine and methionine metabolisms | 12 | |
| 13 | DNA replication | | 15 |
| 14 | Fatty acid degradation | | 6 |
| 15 | Fatty acid metabolism | 18 | 6 |
| 16 | Galactose metabolism | | 6 |
| 17 | Glycerolipid metabolism | 12 | |
| 18 | Histidine metabolism | 12 | |
| 19 | Homologous recombination | | 9 |
| 20 | Lysine biosynthesis | 9 | |
| 21 | Lysine degradation | 12 | |
| 22 | Meiosis - yeast | | 15 |
| 23 | Metabolic pathways | 120 | 27 |
| 24 | Mismatch repair | | 6 |
| 25 | Monobactam biosynthesis | 6 | |
| 26 | Nucleotide excision repair | | 6 |

TABLE 2-continued

Results of comparison/analysis of transcriptomes of parent strain and DAME-tolerant mutant strain (ES5)

| No | Pathway | No of Upregulated Genes | No of Downregulated Genes |
|---|---|---|---|
| 27 | Pantothenate and CoA biosynthesis | 12 | |
| 28 | Pentose and glucuronate interconversions | | 6 |
| 29 | Peroxisome | 27 | 6 |
| 30 | Pyruvate metabolism | 18 | |
| 31 | Starch and sucrose metabolisms | | 9 |
| 32 | Steroid biosynthesis | 9 | |
| 33 | Tryptophan metabolism | 9 | |
| 34 | Ubiquinone and other terpenoid-quinone biosynthesis | 9 | |
| 35 | Valine, leucine and isoleucine biosynthesis | 12 | |
| 36 | Valine, leucine and isoleucine degradation | 15 | 6 |
| | Total | 453 | 147 |

[Example 5] Whole Base Sequencing of DAME-Tolerant Mutant Strain (ES5) and Searching for Candidate Genes Associated with Tolerance Improvement To identify the genes associated with the DAME tolerance improvement of the ES5 strain obtained by the evolutionary engineering method, whole base sequencing of the ES5 strain was performed. Genomic DNA extraction for whole base sequencing was performed using a DNA isolation kit (Epicentre, Madison, WI, USA). The whole base sequence was analyzed using an Illumina Hiseq 2500 NGS platform (DNA Link USA, INC., San Diego, CA, USA).

A total of 13,256,614 reads, which covered approximately 87.98% of the whole base sequence, were obtained through the whole base sequencing, and then aligned using Picard tool 1.128 software. The aligned sequences were annotated using SNPEff 4.1 (GRCh 37.75), and mapped using BWA 7.12 software. In this case, the SNP DB was deleted by dbSNP138 software. Finally, the genes in which mutations occurred were identified by comparing the genes obtained through the NCBI, Uniprot, KEGG databases.

As a result, it was confirmed that the mutations occurred in a total of 770 genes and a total of 106 mutant genes excluding the genes whose function was not identified were obtained. Among these, the genes LIP1 (lipase, Uniprot.ID: C5M8S7), FAT1 (Fatty Acid Transport Protein, Uniprot.ID: C5M964), MRP1 (Multidrug Resistance Protein CDR1, Uniprot.ID: C5M804), which were expected to be involved in the improvement of tolerance to cytotoxic substrates and be associated with an increase in amount of sebacic acid production, were selected and named LIP1 (SEQ ID NO: 1), FAT1 (SEQ ID NO: 2), and MRP1 (SEQ ID NO: 3), respectively. Their mutant genes were named mtLIP1 (SEQ ID NO: 4), mtFAT1 (SEQ ID NO: 5), and mtMRP1 (SEQ ID NO: 6). The mutation sites of the respective genes are as listed in Tables 3, 4, and 5.

TABLE 3

LIP1 gene (Seq_1-LIP1. Seq_2-mtLIP1)

```
Seq_1    1 atgagatttcttgtattcattacaattattacatggttgaaaactgtatcaactgctcat    60
           |*||||||||||||||||||||||||||||||||||||||||||||||||||||||||||
Seq_2    1 aagagatttcttgtattcattacaattattacatggttgaaaactgtatcaactgctcat    60
```

TABLE 3-continued

LIP1 gene (Seq_1-LIP1. Seq_2-mtLIP1)

```
Seq_1     61 attcctgcaccacttgctgatccaagtagagatgagttttatactccatctccaggtttt   120
             ||||||||||||||||||||||||||||||||||||||||||||||||||||||||||||
Seq_2     61 attcctgcaccacttgctgatccaagtagagatgagttttatactccatctccaggtttt   120

Seq_1    121 gaatacgctactccaggaactattttaaaaatccgtccaactcctcgtgctgttcgtaat   180
             ||||||||||||||||||||||||||||||||||||||||||||||||||||||||||||
Seq_2    121 gaatacgctactccaggaactattttaaaaatccgtccaactcctcgtgctgttcgtaat   180

Seq_1    181 ttattattctttcatgttcctttaaaaaactcttggcaattgttggttagatctcaagat   240
             ||||||||||||||||||||||||||||||||||||||||||||||||||||||||||||
Seq_2    181 ttattattctttcatgttcctttaaaaaactcttggcaattgttggttagatctcaagat   240

Seq_1    241 tcttttggtgaacctaatgctatagttactacaattcttgaacctatgaattcaaatcct   300
             ||||||||||||||||||||||||||||||||||||||||||||||||||||||||||||
Seq_2    241 tcttttggtgaacctaatgctatagttactacaattcttgaacctatgaattcaaatcct   300

Seq_1    301 tcaaaaattttatcttatcaaacttttgaagattcaacttcattaaaatgcgctaccagt   360
             ||||||||||||||||||||||||||||||||||||||||||||||||||||||||||||
Seq_2    301 tcaaaaattttatcttatcaaacttttgaagattcaacttcattaaaatgcgctaccagt   360

Seq_1    361 tataattatcaagttggtattccaccatttggaaatgttgctacccaatttgaaatgaaa   420
             ||||||||||||||||||||||||||||||||||||||||||||||||||||||||||||
Seq_2    361 tataattatcaagttggtattccaccatttggaaatgttgctacccaatttgaaatgaaa   420

Seq_1    421 tttataattcctgctttaaataaaggatattttgtaattagtcctgattatgaaggacca   480
             ||||||||||||||||||||||||||||||||||||||||||||||||||||||||||||
Seq_2    421 tttataattcctgctttaaataaaggatattttgtaattagtcctgattatgaaggacca   480

Seq_1    481 agaggtgcatttactgttggtgcacaagcagcacatgcagtattggattctattcgtgct   540
             ||||||||||||||||||||||||||||||||||||||||||||||||||||||||||||
Seq_2    481 agaggtgcatttactgttggtgcacaagcagcacatgcagtattggattctattcgtgct   540

Seq_1    541 gtattgaattctgggtctataacttctattgatccagatgctaaagttgcaatgtgggt   600
             ||||||||||||||||||||||||||||||||||||||||||||||||||||||||||||
Seq_2    541 gtattgaattctgggtctataacttctattgatccagatgctaaagttgcaatgtgggt   600

Seq_1    601 tattctggaggatccttagcatcaagttgggcagctgtaatgcaacctgaatatgcacct   660
             ||||||||||||||||||||||||||||||||||||||||||||||||||||||||||||
Seq_2    601 tattctggaggatccttagcatcaagttgggcagctgtaatgcaacctgaatatgcacct   660

Seq_1    661 gaattatcaaataatttaataggtgctgcctt-gggaggatttgttactaatataactgc   719
             |||||*||||||||||||||||| ||||||*|||||||||||||||||||||||||||||
Seq_2    661 gaattgtcaaataatttaataggtgttgccttggggaggatttgttactaatataactgc   720

Seq_1    720 tgttgctgaatattctgatagaactccactttctggtcttgttccagtagcacttaatgg   779
             ||||||||||||||||||||||||||||||||||||||||||||||||||||||||||||
Seq_2    721 tgttgctgaatattctgatagaactccactttctggtcttgttccagtagcacttaatgg   780

Seq_1    780 attagccaatgaatatccattggttagacaattgcttaatcaagaaataagtcctaaaaa   839
             ||||||||||||||||||||||||||||||||||||||||||||||||||||||||||||
Seq_2    781 attagccaatgaatatccattggttagacaattgcttaatcaagaaataagtcctaaaaa   840

Seq_1    840 aaatgcaagttttcatcgtggagttcaaaaatgttttcttcctgctatagcttatttag   899
             ||||||||||||||||||||||||||||||||||||||||||||||||||||||||||||
Seq_2    841 aaatgcaagttttcatcgtggagttcaaaaatgttttcttcctgctatagcttatttag   900

Seq_1    900 aggaagaactattcttggtagaaataatgaaaagaaagcaatgtttcctaatggatggca   959
             ||||||||||||||||||||||||||||||||||||||||||||||||||||||||||||
Seq_2    901 aggaagaactattcttggtagaaataatgaaaagaaagcaatgtttcctaatggatggca   960

Seq_1    960 tttccttgataatcct-gattttttgacattcttgataaaataatttgatttcttata   1018
             ||||| ||||||||||**||||||||||||||||||||||||||||||||||||||||||
Seq_2    961 tttacttgataatcccggattttttgaaattcttgataaaataattcgatttcttata   1020

Seq_1   1019 acgcaattccaaaaattccaatatttgtatatcatggctacaaa--gatggcgttgttcc   1076
             ||||| ||||||||||||||||||||||||||||||||||||**|||||||||||||||
Seq_2   1021 acgcacttccaaaaattccaatatttgtatatcatggcacaaaaacgatggagttgttcc   1080

Seq_1   1077 gatttcctatgctcataaaattttcgataaatggtgtgatgagggaattgaatcgtttga   1136
             ||||||||||||||||||||||||||||||||||||||||||||||||||||||||||||
Seq_2   1081 gatttcctatgctcataaaattttcgataaatggtgtgatgagggaattgaatcgtttga   1140

Seq_1   1137 atttgcagaatctttaactactggccatatattggaaacttttactggtgctgcagccgc   1196
             ||||||||||||||||||||||||||||||||||||||||||||||||||||||||||||
Seq_2   1141 atttgcagaatctttaactactggacatatattggaaccttttactggtgctgcagccgc   1200
```

TABLE 3-continued

LIP1 gene (Seq_1-LIP1. Seq_2-mtLIP1)

```
Sca1 1197 ttggacttggttacaaaaacgctttgatgatgtacctccatataatggttgtttccatac 1256
          ||||||||||||||||||||||||||||||||||||||||||||||||||||||||||||
Seq_2 1201 ttggacttggttacaaaaacgatttgatgatgtacctccatataatggttgtttccatac 1260

Seq_1 1257 aagacgactcactaatttgaagtacacgggagcatcaaagagtataattgattattacga 1316
           ||||||||||||||||||||||||||||||||||||||||||||||||||||||||||||
Seq_2 1261 aagaagactcactaatttgaagtacacgggagcatcaaagagtataattgattattacga 1320

Seq_1 1317 tgggttgtttaaagaaagcttcactgtgaagaatagtacctatcttgtctag 1368
           ||||||||||||||||||||||||||||||||||||||||||||||||||||
Seq_2 1321 tgggttgtttaaagaaagcttcactgtgaagaatagtacctatcttgtctag 1372
```

TABLE 4

FAT1 gene (Seq_1-FAT1. Seq_2-mFAT1)

```
Seq_1    1 atgtcaggattagaaattgctgcagctgccgttcttggtagtcagttattagaagccaaa   60
           ||||||||||||||||||||||||||||||||||||||||||||||||||||||||||||
Seq_2    1 atgtcaggattagaaattgctgcagctgccgttcttggtagtcagttattagaagccaaa   60

Seq_1   61 tatttaatttccgatgatgtactgttggccaaaacagttgctcttaatgcacttccatat  120
           ||||||||||||||||||||||||||||||||||||||||||||||||||||||||||||
Seq_2   61 tatttaatttccgatgatgtactgttggccaaaacagttgctcttaatgcacttccatat  120

Seq_1  121 ttatggaaagcctccaggggtaaagcttcatattggtatttctttgaaaaatcagtattt  180
           ||||||||||||||||||||||||||||||||||||||||||||||||||||||||||||
Seq_2  121 ttatggaaagcctccaggggtaaagcttcatattggtatttctttgaaaaatcagtattt  180

Seq_1  181 aaaaatccaataataaagcattggcatttccaagaccaagaaagaatgcaccaccacca   240
           ||||||||||||||||||||||||||||||||||||||||||||||||||||||||||||
Seq_2  181 aaaaatccaataataaagcattggcatttccaagaccaagaaagaatgcaccaccacca   240

Seq_1  241 aaggttgatgatgaaggattttcaaatttatgacgatcaatttgacctagaagaatatacc  300
           ||||||||||||||||||||||||||||||||||||||||||||||||||||||||||||
Seq_2  241 aaggttgatgatgaaggattttcaaatttatgacgatcaatttgacctagaagaatatacc  300

Seq_1  301 tataaggaattgtatgacatggttttgaaatactcttacattttgaaacatgaatatggt  360
           ||||||||||||||||||||||||||||||||||||||||||||||||||||||||||||
Seq_2  301 tataaggaattgtatgacatggttttgaaatactcttacattttgaaacatgaatatggt  360

Seq_1  361 gttactgcaaatgatactattggtgtttcttgtatgaataaaccacttttcattgtttta  420
           ||||||||||||||||||||||||||||||||||||||||||||||||||||||||||||
Seq_2  361 gttactgcaaatgatactattggtgtttcttgtatgaataaaccacttttcattgtttta  420

Seq_1  421 tggttggccttatggaatattggtgccttgccagcattttgaatttcaacaccaaagat  480
           ||||||||||||||||||||||||||||||||||||||||||||||||||||||||||||
Seq_2  421 tggttggccttatggaatattggtgccttgccagcattttgaatttcaacaccaaagat  480

Seq_1  481 aaaccattgattcactgtcttaaaattgtcaatgctagtcaagttttcgttgatcctgat  540
           ||||||||||||||||||||||||||||||||||||||||||||||||||||||||||||
Seq_2  481 aaaccattgattcactgtcttaaaattgtcaatgctagtcaagttttcgttgatcctgat  540

Seq_1  541 tgtgatgctccaatcaaagatactgaatctcaaattaaagaggaattaccacatgttaga  600
           ||||||||||||||||||||||||||||||||||||||||||||||||||||||||||||
Seq_2  541 tgtgatgctccaatcaaagatactgaatctcaaattaaagaggaattaccacatgttaga  600

Seq_1  601 ataaattacattgatgaatttgctttgt-ttgatagattaagactcaagtctactccaaa  659
           ||||||||||||||||||||||||||||*|||||||||||||||||||||||||||||||
Seq_2  601 ataaattacattgatgaatttgctttgtattgatagattaagactcaagtctactccaaa  660

Seq_1  660 atacagagctgaagatagtactagaagaccaacagataccgattcttccgcctgtgcgtt  719
           ||||||||||||||||||||||||||||||||||||||||||||||||||||||||||||
Seq_2  661 atacagagctgaagatagtactagaagaccaacagataccgattcttccgcctgtgcgtt  720

Seq_1  720 gatctatacatcaggtaccactggtttaccaaaagcaggtatcatgtcttggagaaaagc  779
           ||||||||||||||||||||||||||||||||||||||||||||||||||||||||||||
Seq_2  721 gatctatacatcaggtaccactggtttaccaaaagcaggtatcatgtcttggagaaaagc  780

Seq_1  780 attcatggcttctgttttctttggccatattatgaaaattaagaatgattccaatgtttt  839
           |||||||||||||||||*||||||||||||||||||||||||||||||||||||||||||
Seq_2  781 attcatggcttctgtttccttggccatattatgaaaattaagaatgattccaatgtttt  840

Seq_1  840 aacagctatgccattgtatcattcaacagctgctatgttgggtttgtgtcctactttaat  899
           ||||*|||||||||||||||||||||||||||||||||||||||||||||||||||||||
```

TABLE 4-continued

FAT1 gene (Seq_1-FAT1. Seq_2-mFAT1)

```
Seq_2   841 tacagttatgccattgtatcattcaacagctgctatgttgggtttgtgtcctactttaat    900

Seq_1   900 tgttggtggttgtgtttctgtttctcaaaattctcagccacttcattctggactcaagc    959
            ||||||||||||||||||||||||||||||||||||||||||||||||||||||||||||
Seq_2   901 tgttggtggttgtgtttctgtttctcaaaaattctcagccacttcattctggactcaagc    960

Seq_1   960 tagattatgtggtgccacacatattcaatatgttggtgaagtttgtcgttattgttaaa   1019
            ||||||||||||||||||||||||||||||||||||||||||||||||||||||||||||
Seq_2   961 tagattatgtggtgccacacatattcaatatgttggtgaagtttgtcgttattgttaaa   1020

Seq_1  1020 ctcaaaacatcacccagatcaagatagacacaatgttaaaattgcctatggtaatggatt   1079
            ||||||||||||||||||||||||||||||||||||||||||||||||||||||||||||
Seq_2  1021 ctcaaaacatcacccagatcaagatagacacaatgttaaaattgcctatggtaatggatt   1080

Seq_1  1080 acgtccagatatatggtctgaattcaagagaagattccacattgaaggtattggggaatt   1139
            ||||||||||||||||||||||||||||||||||||||||||||||||||||||||||||
Seq_2  1081 acgtccagatatatggtctgaattcaagagaagattccacattgaaggtattggggaatt   1140

Seq_1  1140 ttatgcagctactgaatctccaattgccactacaaacttacaatacggtgaatatggtgt   1199
            ||||||||||||||||||||||||||||||||||||||||||||||||||||||||||||
Seq_2  1141 ttatgcagctactgaatctccaattgccactacaaacttacaatacggtgaatatggtgt   1200

Seq_1  1200 aggtgcctgtcgtaaatatggttcacttattagtttattgttatctacccaacaaaaatt   1259
            ||||||||||||||||||||||||||||||||||||||||||||||||||||||||||||
Seq_2  1201 aggtgcctgtcgtaaatatggttcacttattagtttattgttatctacccaacaaaaatt   1260

Seq_1  1260 ggccaagatggatccagaagatgaaagtgaaatttataaggatccaaaaactggatttg   1319
            ||||||||||||||||||||||||||||||||||||||||||||||||||||||||||||
Seq_2  1261 ggccaagatggatccagaagatgaaagtgaaatttataaggatccaaaaactggatttg   1320

Seq_1  1320 tgttgaagctgcatataatgaacctggtgaattgttgatgagaattttaaatcctaatga   1379
            ||||||||||||||||||||||||||||||||||||||||||||||||||||||||||||
Seq_2  1321 tgttgaagctgcatataatgaacctggtgaattgttgatgagaattttaaatcctaatga   1380

Seq_1  1380 tattcaaaaatcattccaaggttattatggtaacaaatctgctaccaatagcaaaattct   1439
            ||||||||||||||||||||||||||||||||||||||||||||||||||||||||||||
Seq_2  1381 tattcaaaaatcattccaaggttattatggtaacaaatctgctaccaatagcaaaattct   1440

Seq_1  1440 cacgaatgttttcaaaaaggagatgcttggtatagaagtggtgacttgttgaaaatgga   1499
            ||||||||||||||||||||||||||||||||||||||||||||||||||||||||||||
Seq_2  1441 cacgaatgttttcaaaaaggagatgcttggtatagaagtggtgacttgttgaaaatgga   1500

Seq_1  1500 tgaacatcaattgttgtattttgttgatagattgggtga----taccttccgttggaaat   1555
            ||||||||||||||||||||||||||||||||||||||****||||||||||||||||||
Seq_2  1501 tgaacatcaattgttgtattttgttgatagattgggtgagaaataccttccgttggaaat   1560

Seq_1  1556 cagaaaatgtttcagcaactgaagttgaaaatgagttgatgggatctaaagcattgaaac   1615
            ||||||||||||||||||||||||||||||||||||||||||||||||||||||||||||
Seq_2  1561 cagaaaatgtttcagcaactgaagttgaaaatgagttgatgggatctaaagcattgaaac   1620

Seq_1  1616 aatctgttgttgttggtgttaaagttcca--aatcacgaaggtagagcttgttttgctgt   1673
            |||||||||||||||||||||||||||||**|||||||||||||||||||||||||||||
Seq_2  1621 aatctgttgttgttggtgttaaagttccaggaatcacgaaggtagagcttgttttgctgt   1680

Seq_1  1674 atgtgaagcaaaagatgatttaactcatgaagatattttgaaattgattcatggacatgt   1733
            ||||||||||||||||||||||||||||||||||||||||||||||||||||||||||||
Seq_2  1681 atgtgaagcaaaagatgatttaactcatgaagatattttgaaattgattcatggacatgt   1740

Seq_1  1734 tactaaatcgttaccagtttatgcacaacctgcattcattaaaatcggatccattgaagc   1793
            ||||||||||||||||||||||||||||||||||||||||||||||||||||||||||||
Seq_2  1741 tactaaatcgttaccagtttatgcacaacctgcattcattaaaatcggatccattgaagc   1800

Seq_1  1794 ttctcataatcataaagttccaaagaatcaatttaagaatcaaaaattaccaaaaggtga   1853
            ||||||||||||||||||||||||||||||||||||||||||||||||||||||||||||
Seq_2  1801 ttctcataatcataaagttccaaagaatcaatttaagaatcaaaaattaccaaaaggtga   1860

Seq_1  1854 agatggtaaagacttgatttactggttgaatggtgataaatatcaagagttgactgaaga   1913
            ||||||||||||||||||||||||||||||||||||||||||||||||||||||||||||
Seq_2  1861 agatggtaaagacttgatttactggttgaatggtgataaatatcaagagttgactgaaga   1920

Seq_1  1914 ggattggtctttgatctgtactggtaaagccaaattgtaa                      1953
            ||||||||||||||||||||||||||||||||||||||||
Seq_2  1921 ggattggtctttgatctgtactggtaaagccaaattgtaa                      1960
```

TABLE 5

MRP1 gene (Seq_1-MRP1, Seq_2-mtMRP1)

```
Seq_1    1 atgggagaaataaccccaactgacaaaagcgaagaccagtcaatggttaatgcatatcat   60
           ||||||||||||||||||||||||||||||||||||||||||||||||||||||||||||
Seq_2    1 atgggagaaataaccccaactgacaaaagcgaagaccagtcaatggttaatgcatatcat   60

Seq_1   61 ggatttgatactcatgcatcagaagatatacaagatttagccaaaacttttactcatcat  120
           ||||||||||||||||||||||||||||||||||||||||||||||||||||||||||||
Seq_2   61 ggatttgatactcatgcatcagaagatatacaagatttagccaaaacttttactcatcat  120

Seq_1  121 tcaattggcgatggtactgatggtttacaaagatatcttacaaatatgacagaagtacca  180
           ||||||||||||||||||||||||||||||||||||||||||||||||||||||||||||
Seq_2  121 tcaattggcgatggtactgatggtttacaaagatatcttacaaatatgacagaagtacca  180

Seq_1  181 ggtataaatccttacaccgaagatatttacactagtgaccaattgaatccagactcagat  240
           ||||||||||||||||||||||||||||||||||||||||||||||||||||||||||||
Seq_2  181 ggtataaatccttacaccgaagatatttacactagtgaccaattgaatccagactcagat  240

Seq_1  241 aattttaatgcaaagttttggatcaagaacttgagaaaattgtatgattcagatccagat  300
           ||||||||||||||||||||||||||||||||||||||||||||||||||||||||||||
Seq_2  241 aattttaatgcaaagttttggatcaagaacttgagaaaattgtatgattcagatccagat  300

Seq_1  301 tattacaagccatcaagattgggagttgcctatagagatttaagagcttatggtgtggcc  360
           ||||||||||||||||||||||||||||||||||||||||||||||||||||||||||||
Seq_2  301 tattacaagccatcaagattgggagttgcctatagagatttaagagcttatggtgtggcc  360

Seq_1  361 aatgattctgattaccagcccactgtggcaaacgcggtctggaagtttatcaaagaggga  420
           ||||||||||||||||||||||||||||||||||||||||||||||||||||||||||||
Seq_2  361 aatgattctgattaccagcccactgtggcaaacgcggtctggaagtttatcaaagaggga  420

Seq_1  421 ttgcattatttagaaaaaggtgatggctcaaggtattttgatattttaaaatcaatggat  480
           ||||||||||||||||||||||||||||||||||||||||||||||||||||||||||||
Seq_2  421 ttgcattatttagaaaaaggtgatggctcaaggtattttgatattttaaaatcaatggat  480

Seq_1  481 ggaataatgaaaccaggtgaacttacagttgttttaggtagaccaggggctggttgttcc  540
           ||||||||||||||||||||||||||||||||||||||||||||||||||||||||||||
Seq_2  481 ggaataatgaaaccaggtgaacttacagttgttttaggtagaccaggggctggttgttcc  540

Seq_1  541 acattgttgaaaacattggcttcacaaacatatggatttcatattggaaaagaatcaaaa  600
           ||||||||||||||||||||||||||||||||||||||||||||||||||||||||||||
Seq_2  541 acattgttgaaaacattggcttcacaaacatatggatttcatattggaaaagaatcaaaa  600

Seq_1  601 atcagttatgatggtttaactcctcccgaaatcgaaaaaacttatagggggtaatgttgta  660
           ||||||||||||||||||||||||||||||||||||||||||||||||||||||||||||
Seq_2  601 atcagttatgatggtttaactcctcccgaaatcgaaaaaacttatagggggtaatgttgta  660

Seq_1  661 tactctgcagaaacagatgttcattttccacatttgactgtcggacaagtcttggaattt  720
           ||||||||||||||||||||||||||||||||||||||||||||||||||||||||||||
Seq_2  661 tactctgcagaaacagatgttcattttccacatttgactgtcggacaagtcttggaattt  720

Seq_1  721 gctgctagaatgagaacgccacagaacagaggtgaaggtgtagatagagaaacatatgcc  780
           ||||||||||||||||||||||||||||||||||||||||||||||||||||||||||||
Seq_2  721 gctgctagaatgagaacgccacagaacagaggtgaaggtgtagatagagaaacatatgcc  780

Seq_1  781 aaacaccttgctagtgtttatatggctacttatgggttatctcatacaagaaataccaat  840
           |||||||*||*|||||||||||||||||||||||||||||||||||||||||||||||||
Seq_2  781 aaacaccatgttagtgtttatatggctacttatgggttatctcatacaagaaataccaat  840

Seq_1  841 gtgggtaacgattttgtcagaggagtttctggtggtgaaagaaaaagggtctccattgct  900
           ||||||||||||||||||||||||||||||||||||||||||||||||||||||||||||
Seq_2  841 gtgggtaacgattttgtcagaggagtttctggtggtgaaagaaaaagggtctccattgct  900

Seq_1  901 gaagtttcgttgagtggtgcaaatgttcaatgttgggataatgccactaaaggttttggat  960
           |||||||||||||||||||||*||||||||||||||||||||||||||||*||||||||
Seq_2  901 gaagtttcgttgagtggtgcaaacgttcaatgttgggataatgccactaaaggttttggat  960

Seq_1  961 gctgcaaccgcattggaattcatcagagcattgaagacttctgctgctatttttggaaagt 1020
           ||||||||||||||||||||||||||||||||||||||||||||||||||||||||||||
Seq_2  961 gctgcaaccgcattggaattcatcagagcattgaagacttctgctgctatttttggaaagt 1020

Seq_1 1021 accccattgattgctatttatcaatgttcacaagatgcttatgacttgtttgataatgtt 1080
           |||||||||||||||*|||||||||||||||||||||||||||||*||||||||||*|
Seq_2 1021 accccattgattgctacttatcaatgttcacaagatgcttatgacttgtatgataatgct 1080

Seq_1 1081 gtcgttttgtatgaaggtttccaaatttttttttggtaaagccaataaagccaaggagtat 1140
           ||||||||||||||||||||||||||||||||||||||||||||||||||||||||||||
Seq_2 1081 gtcgttttgtatgaaggtttccaaatttttttttggtaaagccaataaagccaaggagtat 1140

Seq_1 1141 tttgtaaacatgggatacaagtgtcctcaaagacaaaccactgctgacttttttaacttca 1200
           ||||||||||||||||||||||||||||||||||*|||||||*|||||||||||||||||
```

TABLE 5-continued

MRP1 gene (Seq_1-MRP1, Seq_2-mtMRP1)

```
Seq_2  1141  tttgtaaacatgggatacaagtgtcctcatagacaaaacactgctgacttttttaacttca  1200

Seq_1  1201  ttgactaatccagctgaaagagagccattaccaggttatgagaataaagtcccaaggact  1260
             ||||||||||||||||||||||||||||||||||||||||||||||||||||||||||||
Seq_2  1201  ttgactaatccagctgaaagagagccattaccaggttatgagaataaagtcccaaggact  1260

Seq_1  1261  cctcaagaatttgaagcatattggaagaaatccccagagtatactgcattggttaatgaa  1320
             ||||||||||||||||||||||||||||||||||||||||||||||||||||||||||||
Seq_2  1261  cctcaagaatttgaagcatattggaagaaatccccagagtatactgcattggttaatgaa  1320

Seq_1  1321  attgattcatatttcattgagtgtgagaaattaaacaccagacaactctaccaagattca  1380
             |||  |||||||||||||||||||||||||||||||||||||||||||||||||||||||
Seq_2  1321  attcattcatatttcattgagtgtgagaaattaaacaccagacaactctaccaagattca  1380

Seq_1  1381  catgttgcaagacaatccaacaatattcgtccatcttcaccatatactgtatcattttc  1440
             ||||||||||||||||||||||||||||||||||||||||||||||||||||||||||||
Seq_2  1381  catgttgcaagacaatccaacaatattcgtccatcttcaccatatactgtatcattttc  1440

Seq_1  1441  atgcaagtaaagtatgttatacaaagaaatttcctccgtatgaaagctgatccatcgatt  1500
             ||||||||||||||||||||||||||||||||||||||||||||||||||||||||||||
Seq_2  1441  atgcaagtaaagtatgttatacaaagaaatttcctccgtatgaaagctgatccatcgatt  1500

Seq_1  1501  ccgttgactactattttctcacaactagttatgggacttattcttgcctcggtattttac  1560
             ||||||||||||||||||||||||||||||||||||||||||||||||||||||||||||
Seq_2  1501  ccgttgactactattttctcacaactagttatgggacttattcttgcctcggtattttac  1560

Seq_1  1561  aatcttcctgcaacttcaggttcttttttactaccgatccggtgcgctttactttggtttg  1620
             ||||||||||||||||||||||||||||||||||||||||||||||||||||||||||||
Seq_2  1561  aatcttcctgcaacttcaggttcttttttactaccgatccggtgcgctttactttggtttg  1620

Seq_1  1621  ttatttaatgctatttcgtccctacttgaaattattgcccttttttgaagcaagacccatt  1680
             ||||||||||||||||||||||||||||||||||||||||||||||||||||||||||||
Seq_2  1621  ttatttaatgctatttcgtccctacttgaaattattgcccttttttgaagcaagacccatt  1680

Seq_1  1681  gttgagaaacataaaaaatatgcctttatcgtccatcagcagatgcattagcaagtatt  1740
             ||||||||||||||||||||||||||||||||||||||||||||||||||||||||||||
Seq_2  1681  gttgagaaacataaaaaatatgcctttatcgtccatcagcagatgcattagcaagtatt  1740

Seq_1  1741  ataagtgagttaccagttaagttttttcaatccttgtgtttcaacattcctttctatttt  1800
             ||||||||||||||||||||||||||||||||||||||||||||||||||||||||||||
Seq_2  1741  ataagtgagttaccagttaagttttttcaatccttgtgtttcaacattcctttctatttt  1800

Seq_1  1801  atggttaaccttagaagagatgctggtagattcttcttttattggttaattggtatatta  1860
             ||||||||||||||||||||||||||||||||||||||||||||||||||||||||||||
Seq_2  1801  atggttaaccttagaagagatgctggtagattcttcttttattggttaattggtatatta  1860

Seq_1  1861  ggtacattcattatgtcacacttattcagatctattggtgcagtatttactactttagca  1920
             ||||||||||||||||||||||||||||||||||||||||||||||||||||||||||||
Seq_2  1861  ggtacattcattatgtcacacttattcagatctattggtgcagtatttactactttagca  1920

Seq_1  1921  ggtgctatgactccggcggggtgattttattagcaatgatattatttgctggatttgtc  1980
             ||||||||||||||||||||||||||||||||||||||||||||||||||||||||||||
Seq_2  1921  ggtgctatgactccggcggggtgattttattagcaatgatattatttgctggatttgtc  1980

Seq_1  1981  attccatttccaagcatgttgggttggtctaaatggataaaatggataaatcctgtcact  2040
             ||||||||||||||||||||||||||||||||||||||||||||||||||||||||||||
Seq_2  1981  attccatttccaagcatgttgggttggtctaaatggataaaatggataaatcctgtcact  2040

Seq_1  2041  tatttgtttgaatcacttatggtaaacgagtatcataatagagagtttgaatgcagtgat  2100
             ||||||||||||||||||||||||||||||||||||||||||||||||||||||||||||
Seq_2  2041  tatttgtttgaatcacttatggtaaacgagtatcataatagagagtttgaatgcagtgat  2100

Seq_1  2101  ttcgtacctatgggaccaggatatgagaatcttagtcttgaaaataaggtttgttcaagt  2160
             ||||||||||||||||||||||||||||||||||||||||||||||||||||||||||||
Seq_2  2101  ttcgtacctatgggaccaggatatgagaatcttagtcttgaaaataaggtttgttcaagt  2160

Seq_1  2161  ttgggtggcatccctggtagtgcttttgttcaaggtgatgattatttaagacttggatttt  2220
             ||||||||||||||||||||||||||||||||||||||||||||||||||||||||||||
Seq_2  2161  ttgggtggcatccctggtagtgcttttgttcaaggtgatgattatttaagacttggatttt  2220

Seq_1  2221  gccttttctaactcccataagtggagaaattttggtatatctgttgcgtttgctgtgttt  2280
             ||||||||||||||||||||||||||||||||||||||||||||||||||||||||||||
Seq_2  2221  gccttttctaactcccataagtggagaaattttggtatatctgttgcgtttgctgtgttt  2280

Seq_1  2281  cttttgtttctttatgttgcattgactgaactcaataaaggtgctatgcaaaaaggtgaa  2340
             ||||||||||||||||||||||||||||||||||||||||||||||||||||||||||||
Seq_2  2281  cttttgtttctttatgttgcattgactgaactcaataaaggtgctatgcaaaaaggtgaa  2340
```

TABLE 5-continued

MRP1 gene (Seq_1-MRP1, Seq_2-mtMRP1)

```
Seq_1  2341  attgtgttgtttcttagaggatctttgaagaaatacaagagaaactccagtagcgcagat  2400
             ||||||||||||||||||||||||||||||||||||||||||||||||||||||||||||
Seq_2  2341  attgtgttgtttcttagaggatctttgaagaaatacaagagaaactccagtagcgcagat  2400

Seq_1  2401  attgaatccggtaaagaaatagtgaaatttaatttccaagacgaagcagaatcttctaat  2460
             |||||||| ||||||||||||||||||||| |||||||||||||||||||||| ||||||
Seq_2  2401  attgaatcgggtaaagaaatagtgaaatttgatttccaagacgaagcagaatctttctaat  2460

Seq_1  2461  agtgatcgtattgatgaaagggttctacgggcagtgaagaattactaccagacaacaga  2520
             ||||||||||||||||||||||||||||||||||||||||||||||||||||||||||||
Seq_2  2461  agtgatcgtattgatgaaagggttctacgggcagtgaagaattactaccagacaacaga  2520

Seq_1  2521  gaaattttcttttggaagaatttgacatatcaagtcaagattaagaaagaagatagagtc  2580
             ||||||||||||||||||||||||||||||||||||||||||||||||||||||||||||
Seq_2  2521  gaaattttcttttggaagaatttgacatatcaagtcaagattaagaaagaagatagagtc  2580

Seq_1  2581  attttagaccatgttgatggttgggttaaaccaggtcaaattactgcattgatgggtgca  2640
             ||||||||||||||||||||||||||||||||||||||||||||||||||||||||||||
Seq_2  2581  attttagaccatgttgatggttgggttaaaccaggtcaaattactgcattgatgggtgca  2640

Seq_1  2641  tctggtgctggtaagaccactttgttgaattgtttatctgagagagtaactactggtgtt  2700
             ||||||||||||||||||||||||||||||||||||||||||||||||||||||||||||
Seq_2  2641  tctggtgctggtaagaccactttgttgaattgtttatctgagagagtaactactggtgtt  2700

Seq_1  2701  attactgatggtgtgagaatggttaatggtcatgcgctagattcttcgttccaaagatca  2760
             |||||||||||||||||||||||||||||||||| |||||||||||||||||||||||||
Seq_2  2701  attactgatggtgtgagaatggttaatggtcatgcgttagattcttcgttccaaagatca  2760

Seq_1  2761  attggttatgtgcaacaacaagatgttcatttacagacatctacagttagagaagcgttg  2820
             ||||||||||||||||||||||||||||||||||||||||||| ||||||||||||||||
Seq_2  2761  attggttatgtgcaacaacaagatgttcatttacagacatctacagttagagaagcgttg  2820

Seq_1  2821  caattctccgcatatttgagacaatcaaacaaaatatctaagaaggagaaggatgaatat  2880
             ||||||||||||||||||||||||||||||||||||||||||||||||||||||||||||
Seq_2  2821  caattctccgcatatttgagacaatcaaacaaaatatctaagaaggagaaggatgaatat  2880

Seq_1  2821  gttgactacgtcattgacttgttggagatgactaactatgcggatgcattggttggtgtt  2940
             ||||||||||||||||||||||||||||||||||||||||||||||||||||||||||||
Seq_2  2881  gttgactacgtcattgacttgttggagatgactaactatgcggatgcattggttggtgtt  2940

Seq_1  2941  gccggtgaaggtttgaatgttgaacaaagaaagagattaaccatcggtgttgaattagtt  3000
             ||||||||||||||||||||||||||||||||||||||||||||||||||||||||||||
Seq_2  2941  gccggtgaaggtttgaatgttgaacaaagaaagagattaaccatcggtgttgaattagtt  3000

Seq_1  3001  gccaagcctaagttgttactattcttggatgaaccaacttctggtttagactcccaaact  3060
             ||||||||||||||||||||||||||||||||||||||||||||||||||||||||||||
Seq_2  3001  gccaagcctaagttgttactattcttggatgaaccaacttctggtttagactcccaaact  3060

Seq_1  3061  gcctggtctatttgtaagttgatgagaaagttagctgatcatggtcaagctatcttgtgt  3120
             ||||||||||||||||||||||||||||||||||||||||||||||||||||||||||||
Seq_2  3061  gcctggtctatttgtaagttgatgagaaagttagctgatcatggtcaagctatcttgtgt  3120

Seq_1  3121  acaattcatcaaccttccgcacttattatggctgaattcgatagattgttgttttttgcaa  3180
             ||||||||||||||||||||||||||||||||||||||||||||||||||||||||||||
Seq_2  3121  acaattcatcaaccttccgcacttattatggctgaattcgatagattgttgttttttgcaa  3180

Seq_1  3181  aagggtggtagaactgcttattttggtgacttgggtaaaaactgtcaaaccatgattgac  3240
             ||||||||||||||||||||||||||||||||||||||||||||||||||||||||||||
Seq_2  3181  aagggtggtagaactgcttattttggtgacttgggtaaaaactgtcaaaccatgattgac  3240

Seq_1  3241  tactttgaaaaacacggagcagatccatgtcccaaagaagccaatccagcagaatggatg  3300
             ||||||||||||||||||||||||||||||||||||||||||||||||||||||||||||
Seq_2  3241  tactttgaaaaacacggagcagatccatgtcccaaagaagccaatccagcagaatggatg  3300

Seq_1  3301  ttggaagttgttggtgccgctccaggctcccatgctaaacaggactattttgaagtttgg  3360
             ||||||||||||||||||||||||||||||||||||||||||||||||||||||||||||
Seq_2  3301  ttggaagttgttggtgccgctccaggctcccatgctaaacaggactattttgaagtttgg  3360

Seq_1  3361  agaaactctgacgaatatagagctgttcaaaatgaaatcacccatatggaaactgaatta  3420
             ||||||||||||||||||||||||||||||||||||||||||||||||||||||||||||
Seq_2  3361  agaaactctgacgaatatagagctgttcaaaatgaaatcacccatatggaaactgaatta  3420

Seq_1  3421  gttaaattaccaagagatgaagatcccgaagcacttttgaaatacgctgcacccatttgg  3480
             ||||||||||||||||||||||||||||||||||||||||||||||||||||||||||||
Seq_2  3421  gttaaattaccaagagatgaagatcccgaagcacttttgaaatacgctgcacccatttgg  3480

Seq_1  3481  aaacaatatttgcttgttagttggagggcgattgtacaagattggagatcacctggatat  3540
             ||||||||||||||||||||||||||||||||||||||||||||||||||||||||||||
```

TABLE 5-continued

MRP1 gene (Seq_1-MRP1, Seq_2-mtMRP1)

```
Seq_2  3481  aaacaatatttgcttgttagttggagggcgattgtacaagattggagatcacctggatat  3540

Seq_1  3541  atatactccaaattttcttgattatcgtgtcatctatattgattggattttcattttt   3600
             ||||||||||||||||||||||||||||||||||||||||||||||||||||||||||||
Seq_2  3541  atatactccaaattttcttgattatcgtgtcatctatattgattggattttcattttt   3600

Seq_1  3601  aaagccaaaaatacagttcaagggttgacgaatcaaatgcttgctatatttatgttcaca  3660
             ||||||||||||||||||||||||||||||||||||||||||||||||||||||||||||
Seq_2  3601  aaagccaaaaatacagttcaagggttgacgaatcaaatgcttgctatatttatgttcaca  3660

Seq_1  3661  gttcaattcacaactattattgaccaaatgttgccattttttgttcgacaacgtgaggtg  3720
             ||||||||||||||||||||||||||||||||||||||||||||||||||||||||||||
Seq_2  3661  gttcaattcacaactattattgaccaaatgttgccattttttgttcgacaacgtgaggtg  3720

Seq_1  3721  tatgaggttagagaagcaccttccagaacatatagttgggttgccttcattacaggtcaa  3780
             ||||||||||||||||||||||||||||||||||||||||||||||||||||||||||||
Seq_2  3721  tatgaggttagagaagcaccttccagaacatatagttgggttgccttcattacaggtcaa  3780

Seq_1  3781  ataacttcagagcttccttatcaaataattgttggaacgattgctttcttctgctggtac  3840
             ||||||||||||||||||||||||||||||||||||||||||||||||||||||||||||
Seq_2  3781  ataacttcagagcttccttatcaaataattgttggaacgattgctttcttctgctggtac  3840

Seq_1  3841  tatcctgttggattatataccaatgctgaacctacacatagtgtgactgaacgtggtgcc  3900
             ||||||||||||||||||||||||||||||||||||||||||||||||||||||||||||
Seq_2  3841  tatcctgttggattatataccaatgctgaacctacacatagtgtgactgaacgtggtgcc  3900

Seq_1  3901  ttgatgtggttgtttattacttcattttttgtttacacatcaacatttggtcaattatgt  3960
             ||||||||||||||||||||||||||||||||||||||||||||||||||||||||||||
Seq_2  3901  ttgatgtggttgtttattacttcattttttgtttacacatcaacatttggtcaattatgt  3960

Seq_1  3961  atgtcattcaatgaagatattgaaaatgctggaactgttgctgctacattattcaccttg  4020
             ||||||||||||||||||||||||||||||||||||||||||||||||||||||||||||
Seq_2  3961  atgtcattcaatgaagatattgaaaatgctggaactgttgctgctacattattcaccttg  4020

Seq_1  4021  tgtttgatattttgtggtgttatggttgttccagagaatatgccacgatttggatttttc  4080
             ||||||||||||||||||||||||||||||||||||||||||||||||||||||||||||
Seq_2  4021  tgtttgatattttgtggtgttatggttgttccagagaatatgccacgatttggatttttc  4080

Seq_1  4081  atgtacagatgtaatccatttacttatatgattcaaggtgttctttcaacgggattagct  4140
             ||||||||||||||||||||||||||||||||||||||||||||||||||||||||||||
Seq_2  4021  atgtacagatgtaatccatttacttatatgattcaaggtgttctttcaacgggattagct  4140

Seq_1  4141  cgcaataaagttgtttgtgctgcaagagaacttgttctgcttcaaccaccaaaaggtcaa  4200
             ||||||||||||||||||||||||||||||||||||||||||||||||||||||||||||
Seq_2  4141  cgcaataaagttgtttgtgctgcaagagaacttgttctgcttcaaccaccaaaaggtcaa  4200

Seq_1  4201  acttgttcttcattcttggatccttatatcagtgtggctggaggttattatttacctaat  4260
             ||||||||||||||||||||||||||||||||||||||||||||||||||||||||||||
Seq_2  4201  acttgttcttcattcttggatccttatatcagtgtggctggaggttattatttacctaat  4260

Seq_1  4261  aatgatggaacttgttcattctgttcagtagataatactgatatgtttttacatcgtatc  4320
             || |||||||||||||||||||||||||||||||||||||||||||||||||||||||||
Seq_2  4261  aacgatggaacttgttcattctgttcagtagataatactgatatgtttttacatcgtatc  4320

Seq_1  4321  catgccttatacagtgagagatggagaaattttggattatttattacattcattgtgatt  4380
             ||||||||||||||||||||||||||||||||||||||||||||||||||||||||||||
Seq_2  4321  catgccttatacagtgagagatggagaaattttggattatttattacattcattgtgatt  4380

Seq_1  4381  aatgttgtcttgactgtattcttttattggttagctagggtaccaaaagggtcaagatca  4440
             |||||||||||||||||||||||| |||||||||||||||||||||||||||||||||||
Seq_2  4381  aatgttgtcttgactgtattctttttattggttagctagggtaccaaaagggtcaagatca  4440

Seq_1  4441  aagactaaaaagtga                                               4455
             |||||||||||||||
Seq_2  4441  aagactaaaaagtga                                               4455
```

[Example 6] Manufacture and Phenotypic Change of Strain Overexpressing mtLIP1, mtFAT1, and mtMRP1 Genes

TABLE 6

List of primers used to clone a tolerance gene

| SEQ ID NO | Primers | 5'-3' sequence |
|---|---|---|
| pADH2 promotor cloning in PRS420 | | |
| 7 | ADHpro_F | AAACTCGAGTCTAGCTCCCTAACATGTAGGT (XhoI) |
| 8 | ADHpro_R | AAAGTCGACAGTTGATTGTATGCTTGGTATAGCTT |
| pADH2 terminator cloning in PRS420 | | |
| 9 | ADHter_F | AAAGTCGACTCTAGATAAGCGAATTTCTTATGATTTATGAT TTTTA (SalI-XbaI) |
| 10 | ADHter_R | AAAGCGGCCGCGTGTGGAAGAACGATTACAACAG (NotI) |
| Individual cloning | | |
| 11 | LIP1_F | AAAGTCGACATGAGATTTCTTGTATTCATTACAATTATTAC ATGGTTGAAAAC (SalI) |
| 12 | LIP1_R | AAATCTAGAGTGGTGGTGGTGGTGGACAAGATAGGTA CTATTCTTCACAGTGAAGCTT (XbaI) |
| 13 | FAT1_F | AAAGTCGACATGTCAGGATTAGAAATTGCTGCAGCTGCC (SalI) |
| 14 | FAT1_R | AAATCTAGACAATTTGGCTTTACCAGTACAGATCAAAGAC CA (XbaI) |
| 15 | MRP1_F | AAAGTCGACATGGGAGAAATAACCCCAACTGACAAAAGC G (SalI) |
| 16 | MRP1_R | AAATCTAGACTTTTTAGTCTTGACCCTTTTGGTACC (XbaI) |
| Combination cloning | | |
| 17 | P1_F | AAAGGATCCTCTAGCTCCCTAACATGTAGGT (BamHI) |
| 18 | P1_R | AAAGTCGACAGTTGATTGTATGCTTGGTATAGCTT (SalI) |
| 19 | P2_F | AAAGTCGACCACGTGTCTAGCTCCCTAACATGTAGGT (SalI-PmlI) |
| 20 | P2_R | AAAGCGGCCGCAGTTGATTGTATGCTTGGTATAGCTT (NotI) |
| 21 | P3_F | AAAGTCGACTAAGCGAATTTCTTATGATTTATGATTTTTA (SalI) |
| 22 | P3_R | AAACACGTGGTGTGGAAGAACGATTACAACAG (PmlI) |
| 23 | P4_F | CAGTTGATTGTATGCTTGGTATAGTCGACATGAGATTTCTT GTATTCATTACAATTATT (SalI) |
| 24 | P4_R | GTTAACTAAGCGAATTTCTTATGATTTATGTCGACAGTGGT GGTGGTGGTG (SalI) |
| 25 | P5_F | CAGTTGATTGTATGCTTGGTATAGCGGGCCGCATGTCAGG ATTAGAAATTGCTGCA (NotI) |
| 26 | P5_R | GTTAACTAAGCGAATTTCTTATGATTTATGCGGCCGCACAA TTTGGCTTTACCAGTACAGA (NotI) |
| 27 | P6_F | AAAGCGGCCGCATAAGCGAATTTCTTATGATTTATGATTTT TA (NotI) |
| 28 | P6_R | AAACTCGAGCACGTGAGTTGATTGTATGCTTGGTATAGCTT (XhoI-PmlI) |
| 29 | P7_F | AAACACGTGTAAGCGAATTTCTTATGATTTATGATTTTTA (PmlI) |

TABLE 6-continued

List of primers used to clone a tolerance gene

| SEQ ID NO | Primers | 5'-3' sequence |
|---|---|---|
| 30 | P7_R | AAACTCGAGGTGTGGAAGAACGATTACAACAG (XhoI) |
| 31 | P8_F | CAGTTGATTGTATGCTTGGTATAGCACGTGATGGGAGAAA TAACCCCAACTG (PmlI) |
| 32 | P8_R | GTTAACTAAGCGAATTTCTTATGATTTACACGTGCTTTTTA GTCTTGACCCTTTTGGTA (PmlI) |
| 33 | P9_F | GCTTGATATCGAATTCCTGCAGCCCGGGGGATCCTCTAGCT CCCTAACATGTAGGT (BamHI) |
| 34 | P9_R | GGGGGGCCCGGTACCCAATTCGCCCTCTCGAGGTGTGGAA GAACGATTACAACAG (XhoI) |

Restriction enzyme sites underlined.

TABLE 7

Plasmids used in this study

| Plasmids | Description |
|---|---|
| pET21a | *Escherichia coli* expression vector, Amp$^R$ |
| pAUR123 | Low copy number yeast expression vector, AurA$^R$ for yeast, and Amp$^R$ for *E. coli* |
| pRS420 | High copy number yeast expression vector, G418R for yeast, and Amp$^R$ for *E. coli* |
| Plasmid 5 | pRS420::ADHpro1 |
| Plasmid 6 | pRS420::ADHpro1-ADHter1 |
| Plasmid 7 | Plasmid 6 + LIP1, prs420::adhpro1-LIP1-adhter1 |
| Plasmid 8 | Plasmid 6 + mtlip1, prs420::adhpro1-mtlip1-adhter1 |
| Plasmid 9 | Plasmid 6 + wtfat1, prs420::adhpro1-FAT1-adhter1 |
| Plasmid 10 | Plasmid 6 + mtfat1, prs420::adhpro1-mtfat1-adhter1 |
| Plasmid 11 | Plasmid 6 + wtmrp1, prs420::adhpro1-MRP1-adhter1 |
| Plasmid 12 | plasmid 6 + mtMRP1, pRS420::ADHpro1-mtMRP1-ADHter1 |
| Plasmid 13 | pET21a::ADHpro1 |
| Plasmid 14 | pET21a::ADHpro2 |
| Plasmid 15 | pET21a::ADHter1-ADHpro2 |
| Plasmid 17 | pET21a::ADHpro1-ADHter1-ADHpro2 |
| Plasmid 18 | pET21a::ADHpro1-mtLIP1-ADHter1-ADHpro2 |
| Plasmid 19 | pET21a::ADHpro1-mtLIP1-ADHter1-ADHpro2-mtFAT1 |
| Plasmid 20 | pET21a::ADHter1-ADHpro2-mtFAT1 |
| Plasmid 21 | pET21a::ADHter2-ADHpro3 |
| Plasmid 22 | pET21a::ADHter2-ADHpro3-ADHter3 |
| Plasmid 23 | pET21a::ADHter2-ADHpro3-mtMRP1-ADHter3 |
| Plasmid 24 | pET21a::ADHpro1-mtLIP1-ADHter1-ADHpro2-mtFAT1-ADHter2-ADHpro3-mtMRP1-ADHter3 |
| Plasmid 25 | pRS420::ADHpro1-mtLIP1-ADHter1-ADHpro2-mtFAT1-ADHter2-ADHpro3-mtMRP1-ADHter3 |

[6-1] Manufacture and Phenotypic Change of Strain Overexpressing LIP1 Gene and mtLIP1 Gene To manufacture *C. tropicalis* strains in which the same (mutation-free) gene (LIP1) present in the parent strain and the mutant gene (mtLIP1) screened in Example 5 was separately overexpressed, a cloning experiment was performed as follows. For effective expression of the introduced gene, an ADH promotor (introduced at ADHpro, XhoI/SalI restriction enzyme sites) and an ADH terminator (introduced at ADHter, XbaI/NotI restriction enzyme sites) were amplified using an ADHpro_F/R primer and an ADHter_F/R primer (Table 6), and preferentially introduced into a pRS420 vector to construct a plasmid 6. To obtain a LIP1 gene and an mtLIP1 gene, the genomic DNA extracted from each of the *C. tropicalis* MYA_3404 strain and *C. tropicalis* ES5 strain was amplified using a LIP1-F primer and a LIP1_R primer (Table 5), and the obtained DNA fragments were ligated into SalI and XbaI restriction enzyme sites of the plasmid 6 thus constructed. In this way, the plasmid 7 into which LIP1 was introduced and the plasmid 8 into which mtLIP1 was introduced were finally obtained (Table 7). Then, the plasmids 7 and 8 were transformed into *C. tropicalis* 20962 from which a β-oxidation pathway was deleted, and the *C. tropicalis*_LIP1 and *C. tropicalis*_mtLIP1 strains were finally manufactured.

Phenotypic changes of the strains into which the LIP1 gene and the mtLIP1 gene were separately introduced were compared with that of the control (a *C. tropicalis* strain (β-KO) from which the β-oxidation pathway was deleted). As a result, as shown in FIG. 6, it was confirmed that the growth of the strains into which the LIP1 and mtLIP1 genes were introduced was improved, compared to that of the β-KO strain. In particular, it was confirmed that the strain into which the mtLIP1 gene was introduced had the maximum DCW value (approximately 1.2 g/L). The amounts of DAME consumption of the three strains were compared. As a result, it was confirmed that the β-KO strain hardly consumed DAME, and the LIP1 gene-introduced strain and the mtLIP1 gene-introduced strain had higher amounts of substrate consumption, compared to the control. In particular, it was confirmed that the mtLIP1 gene-introduced strain consumed approximately 70% of the entire substrate in 120 hours (FIG. 7). Finally, the amounts of SA production of the three strains were compared. As a result, it was confirmed that the β-KO strain and the LIP1 gene-introduced strain produced approximately 300 mg/L of sebacic acid, whereas the mtLIP1 gene-introduced strain produced approximately 900 mg/L of sebacic acid (FIG. 8).

From the above-described results, it was confirmed that the LIP1 gene in the *C. tropicalis* strain was a gene that has an influence on the growth of the *C. tropicalis* strain, the consumption of the DAME substrate, and the production of sebacic acid, and that the mutant mtLIP1 gene obtained according to the present invention contributes greatly to an increase in amount of sebacic acid production.

[6-2] Manufacture of mtFAT1 Gene-Introduced Strain and Confirmation of Phenotypic Change Like Example 6-1, the phenotypic changes of the FAT1 gene-introduced strain and the mtFAT1 gene-introduced strain were compared with the control (a *C. tropicalis* strain (β-KO) from which the β-oxidation pathway was deleted). The DNA fragments amplified from the genomic DNA of the *C. tropicalis* MYA_3404 strain and the *C. tropicalis* ES5 strain used in Example 6-1 using the FAT1_F and FAT1_R primers (Table 6) were ligated into the SalI and XbaI restriction enzyme sites of the pRS420 vector present in the plasmid 6 to finally manufacture a plasmid 9 into which the FAT1 gene was introduced and the plasmid 10 into which the mtFAT1 gene was introduced (Table 7). The manufactured plasmids 9 and 10 were then transformed into the *C. tropicalis* 20962 from which the β-oxidation pathway was deleted. Finally, the *C. tropicalis*_FAT1 and *C. tropicalis*_mtFAT1 strains were manufactured.

As a result, as shown in FIG. 9, it was confirmed that there was no significant difference in DCW values between the β-KO strain and the FAT1 gene-introduced strain, but the mtFAT1 gene-introduced strain has a high DCW value (approximately 1.5 g/L), indicating that the growth of the cells was significantly improved due to mutations in the FAT1 gene. The amounts of DAME consumption of the three strains were compared. As a result, it was confirmed that the β-KO strain hardly consumed DAME, and the amount of substrate consumption of the FAT1 gene-introduced strain was not significantly different when compared to that of the β-KO strain, but the mtFAT1 gene-introduced strain had a relatively higher amount of substrate consumption, compared to the control. Also, it was confirmed that the mtFAT1 gene-introduced strain consumed approximately 70% of the entire substrate in 120 hours (FIG. 10). Finally, the amounts of sebacic acid production of the strains were compared. As a result, it was confirmed that the β-KO strain and the FAT1 gene-introduced strain produced approximately 280 mg/L and approximately 384 mg/L of sebacic acid, respectively, after 120 hours of fermentation, whereas the mtFATP1 gene-introduced strain produced approximately 1,275 mg/L of sebacic acid (FIG. 11).

From the above-described results, it was confirmed that, like the LIP1 gene, the FAT1 gene in the *C. tropicalis* strain is a gene that is associated with the growth of the *C. tropicalis* strain, the consumption of the DAME substrate, and the production of sebacic acid, and also confirmed that the mtFAT1 gene obtained according to the present invention contributes greatly to an increase in amount of sebacic acid production.

[6-3] Manufacture of mtMRP1 Gene-Introduced Strain and Confirmation of Phenotypic Change Finally, the phenotypic changes of the MRP1 and mtMRP1 gene-introduced strains were compared with the control (a *C. tropicalis* strain (β-KO) from which the β-oxidation pathway was deleted). Like the previous example, a vector used for cloning was a pRS420 vector into which ADHpro and ADHter used to construct the plasmid 6 were introduced. The vector was amplified using MRP1_F and MRP1_R primers, and then ligated into the SalI/XhoI restriction enzyme site. In this way, plasmids 11 and 12 were constructed, and the constructed plasmids were transformed into *C. tropicalis* 20962 from which the 3-oxidation pathway was deleted to finally manufacture *C. tropicalis*_MRP1 and *C. tropicalis*_mtMRP1 strains.

The MRP1 and mtMRP1 gene-introduced strains manufactured by the method as described above were compared to the β-KO strain used as the control. As a result, it was confirmed that the growth of the MRP1 and mtMRP1 gene-introduced strains was improved. In particular, it was confirmed that the mtMRP1 gene-introduced strain had a high cell mass of approximately 1.5 g/L (FIG. 12). The amounts of DAME consumption of the three strains were compared. As a result, it was confirmed that, after the elapse of 120 hours, the β-KO strain consumed approximately 10% of the substrate, whereas the MRP1 gene-introduced strain consumed approximately 40% of the substrate, and the mtMRP1 gene-introduced strain consumed more than approximately 9 g/L of DAME based on the initial DAME amount of 10 g/L (FIG. 13). The amounts of sebacic acid production of the three strains were compared. As a result, it was confirmed that the β-KO strain and the MRP1 gene-introduced strain produced approximately 280 mg/L and approximately 488 mg/L of sebacic acid, respectively, whereas the mtMRP1 gene-introduced strain produced approximately 1,677 mg/L of sebacic acid, indicating that the amount of sebacic acid production of the mutant strain increased approximately 6-fold, compared to that of the parent strain (FIG. 14).

From the above-described results, it was confirmed that the phenotypic changes of the strains were induced by the introduced MRP1 and mtMRP1 genes, and these genes have a positive influence on the improvement in sebacic acid productivity.

[6-4] Manufacture of Strain (*C. tropicalis* mtSAP7) Producing Large Amount of Sebacic Acid and Production of Sebacic Acid Through High-Density Incubation A strain (*C. tropicalis* mtSAP7) producing a large amount of sebacic acid, into which all the mtLIP1, mtFAT1, and mtMRP1 genes whose effects were confirmed in the previous examples were introduced, was manufactured. To effectively express the three introduced genes, three pairs of ADH promoters (ADHpro1, ADHpro2, and ADHpro3) and ADH terminators (ADHter1, ADHter2, and ADHter3) used to promote the expression of each gene were introduced together. A more specific process for producing a strain was as follows.

(1) A DNA fragment (ADHpro1) amplified from a pAUR123 vector by PCR using the P1_F and P1_R primers was ligated into a BamHI/SAlI restriction enzyme site of a pET21a vector selected for cloning using a T4 DNA ligase to construct a plasmid 13. For PCR, a Q5 High-Fidelity Master mix (BioLabs, Ipswich, MA, USA) was used, and the same reagents were used in all subsequent experiments.

(2) At the same time, a DNA fragment (ADHpro2) amplified from the pAUR123 vector by PCR using P2_F and P2_R primers was ligated into a SalI/NotI restriction enzyme site of the pET21a vector. In this case, in order to promote the later introduction of the strain, a PmlI restriction enzyme sequence (CACGTG) was sequentially added after a restriction enzyme SalI sequence of the forward primer to manufacture a plasmid 14.

(3) Next, a DNA fragment (ADHter1) amplified from the pAUR123 vector using the P3_F and P3_R primers was ligated into a SalI/BtrI restriction enzyme site of the plasmid 14 to manufacture a plasmid 15.

(4) To manufacture a plasmid 16, the previously manufactured plasmid 15 was used as a backbone. A DNA fragment (ADHpro1) amplified using the plasmid 13 as a template and using the P1_F and P1_R primers was ligated into a BamHI/SalI restriction enzyme site of the plasmid 15 to manufacture the plasmid 16.

(5) A DNA fragment (mtLIP1) amplified from the genomic DNA of the *C. tropicalis* ES5 strain using the P4_F and P4_R primers was ligated into a SalI restriction enzyme site between ADHpro1 and ADHter1 of the plasmid 16, thereby manufacturing a plasmid 17.
(6) To introduce the mtFAT1 gene, an mtFAT1 fragment was obtained by PCR using the genomic DNA of the *C. tropicalis* ES5 strain as a template and using the P5_F and P5_R primers. The mtFAT1 fragment was ligated into a NotI restriction enzyme site of the plasmid 17 to manufacture a plasmid 18. Additionally, the amplified mtFAT1 fragment was then introduced into a NotI restriction enzyme site of the plasmid 15 to manufacture the final plasmid, which was named "plasmid 19."
(7) To introduce an additional promoter and terminator, an ADHter2 fragment and an ADHpro3 fragment were obtained by PCR using the plasmid 15 as a template and using the P6_F and P6_R primers. Then, the ADHter2 and ADHpro3 fragments were ligated into a NotI/XhoI restriction enzyme site of a new pET21a vector to obtain a plasmid 20. In this case, a PmlI restriction enzyme site was added prior to the XhoI restriction enzyme site of the P6_R primer, and the resulting construct was used later to manufacture a plasmid 21.
(8) The plasmid 21 was constructed by ligating a DNA fragment (ADHter3), which was amplified from the pAUR123 vector using the P7_F and P7_R primers, into a PmlI/XhoI restriction enzyme site of the previously manufactured plasmid 20.
(9) Finally, to introduce an mtMRP1 gene as the third gene, a plasmid 22 was constructed by ligating a PCR fragment (mtMRP1), which was amplified using the genomic DNA of the *C. tropicalis* ES5 strain as a template and using the P8_F and P8_R primers, into a PmlI restriction enzyme site of the plasmid 21.
(10) Finally, the restriction fragments of the previously manufactured plasmids 18 and 22 were fused to manufacture a plasmid 24 into which all the mtLIP1, mtFAT1, and mtMRP1 genes were introduced. Then, a plasmid 25 was constructed by performing PCR using the plasmid 24 as a template and using the P9_F and P9_R primers and ligating the DNA fragment into a BamHI/XhoI restriction enzyme site of pRS420. The constructed plasmid 25 was transformed into *C. tropicalis* 20962 from which the β-oxidation pathway was deleted to finally manufacture a *C. tropicalis*_mtSAP7 strain. The configuration of the final plasmid 25 and the restriction enzymes used are as shown in FIG. 15.

The *C. tropicalis* strains (mtSAP4 (mtLIP1+mtMRP1), mtSAP5 (mtLIP1+mtFAT1), and mtSAP6 (mtMRP1+mtFAT1)) into which two genes of the mtLIP1, mtFAT1, and mtMRP1 genes were introduced were also manufactured based on the method as described above.

The OD changes, the amounts of substrate consumption, and the amounts of sebacic acid production of the four mutant *C. tropicalis* strains were compared. As a result, it was confirmed that the *C. tropicalis* mtSAP7 strain into which all three mutant genes were introduced had excellent abilities to form cells, consume the substrate, and produce sebacic acid (FIGS. 16, 17, and 18).

To check an effect of the three introduced genes, the manufactured *C. tropicalis*_mtSAP7 strain and the β-oxidation pathway-deleted *C. tropicalis* 20962 (β-KO) strain was fermented under the same conditions. The strains were first incubated in a YP medium supplemented with 100 g/L of glycerol until the OD values of the strains reached 100. After the elapse of 80 hours of incubation, 200 g/L of DAME was added as the substrate, and then incubated at 30° C. for 250 hours.

As a result, no changes in OD values were observed in both of the *C. tropicalis*_mtSAP7 strain and the *C. tropicalis* 20962 strain (a strain from which the β-oxidation pathway was deleted) used as the control (FIG. 19). The amounts of SA production of the two strains were compared. As a result, it was confirmed that the strain used as the control had a maximum amount of sebacic acid production (approximately 27 g/L) at approximately 250 hours, and the mtSAP7 strain produced approximately 110 g/L of sebacic acid after the elapse of approximately 250 hours (FIG. 19).

Based on the study as described above, it was confirmed that the three genes obtained through the whole base sequencing contributed greatly to cell formation, the ability to consume the substrate, and the improvement of sebacic acid productivity. Also, it was confirmed that a process having superior sebacic acid productivity was developed through a high-cell-density bioconversion process using the *C. tropicalis*_mtSAP7 strain, compared to the processes known in the art.

[Example 7] Confirmation of Tolerance of *C. tropicalis* mtSAP7 Strain to FAME Substrate and Production of Dicarboxylic Acid In addition, the *C. tropicalis* mtSAP7 strain manufactured in Example 6-4 was used to check what abilities the strain had to produce sebacic acid from DAME and produce dicarboxylic acids from various FAME substrates, and the abilities of the *C. tropicalis* mtSAP7 strain were then compared with those of the control strain in the same manner as in Example 6.

As a result, as shown in FIG. 20, it was confirmed that the amount of $C_8$ to $C_{12}$ dicarboxylic acid production of the *C. tropicalis* mtSAP7 strain significantly increased in the $C_8$ to $C_{12}$ FAME substrate. Based on these results, it was confirmed that the mutant *C. tropicalis* mtSAP7 strain of the present invention exhibits strong tolerance to the FAME substrates having cytotoxicity, and thus contributes greatly to improved dicarboxylic acid productivity when using FAME as a substrate (FIG. 20).

The invention claimed is:

1. A *Candida tropicalis* strain comprising one or more mutated genes selected from a mutated LIP1 (lipase) gene comprising the nucleotide sequence of SEQ ID NO: 4, a mutated FAT1 (fatty acid transport) gene comprising the nucleotide sequence of SEQ ID NO: 5, and a mutated MRP1 (multidrug resistance protein) gene comprising the nucleotide sequence of SEQ ID NO: 6.

2. The *Candida tropicalis* strain of claim 1, wherein the *Candida tropicalis* strain has a blocked β-oxidation pathway.

3. The *Candida tropicalis* strain of claim 1, wherein the substrate is a fatty acid methyl ester (FAME).

4. The *Candida tropicalis* strain of claim 3, wherein the fatty acid methyl ester substrate comprises one or more selected from $C_6$-$C_{20}$ fatty acid methyl esters.

5. A method for producing a dicarboxylic acid (DCA), the method comprising:
   incubating the *Candida tropicalis* strain defined in claim 1 in a medium with a substrate.

6. The method of claim 5, wherein the substrate is a fatty acid methyl ester (FAME).

7. The method of claim 6, wherein the fatty acid methyl ester comprises one or more selected from $C_6$-$C_{20}$ fatty acid methyl esters.

* * * * *

SEQUENCE LISTING

<160> NUMBER OF SEQ ID NOS: 34

<210> SEQ ID NO 1
<211> LENGTH: 1368
<212> TYPE: DNA
<213> ORGANISM: Candida tropicalis

<400> SEQUENCE: 1

```
atgagatttc ttgtattcat tacaattatt acatggttga aaactgtatc aactgctcat      60
attcctgcac cacttgctga tccaagtaga gatgagtttt tactccatc tccaggtttt      120
gaatacgcta ctccaggaac tattttaaaa atccgtccaa ctcctcgtgc tgttcgtaat     180
ttattattct ttcatgttcc tttaaaaaac tcttggcaat tgttggttag atctcaagat     240
tcttttggtg aacctaatgc tatagttact acaattcttg aacctatgaa ttcaaatcct     300
tcaaaatttt tatcttatca aacttttgaa gattcaactt cattaaaatg cgctaccagt     360
tataattatc aagttggtat tccaccattt ggaaatgttg ctacccaatt tgaaatgaaa     420
tttataattc ctgcttttaa aaaggatat tttgtaatta gtcctgatta tgaaggacca      480
agaggtgcat ttactgttgg tgcacaagca gcacatgcag tattggattc tattcgtgct    540
gtattgaatt ctgggtctat aacttctatt gatccagatg ctaaagttgc aatgtggggt    600
tattctggag atccttagc atcaagttgg gcagctgtaa tgcaacctga atatgcacct     660
gaattatcaa ataatttaat aggtgctgcc ttgggaggat tgttactaa tataactgct    720
gttgctgaat attctgatag aactccactt tctggtcttg ttccagtagc acttaatgga    780
ttagccaatg aatatccatt ggttagacaa ttgcttaatc aagaaataag tcctaaaaaa    840
aatgcaagtt ttcatcgtgg agttcaaaaa tgttttcttc ctgctatagc ttattttaga    900
ggaagaacta ttcttggtag aaataatgaa aagaaagcaa tgtttcctaa tggatggcat    960
ttacttgata atcctgattt ttttgaaatt cttgataaaa ataatttgat ttcttataac   1020
gcaattccaa aaattccaat atttgtatat catggaacaa aagatggagt tgttccgatt   1080
tcctatgctc ataaaatttt cgataaatgg tgtgatgagg gaattgaatc gtttgaattt   1140
gcagaatctt taactactgg acatatattg gaaactttta ctggtgctgc agccgcttgg   1200
acttggttac aaaaacgatt tgatgatgta cctccatata tggttgtttt ccatacaaga   1260
agactcacta atttgaagta cacgggagca tcaaagagta taattgatta ttacgatggg   1320
ttgtttaaag aaagcttcac tgtgaagaat agtacctatc ttgtctag             1368
```

<210> SEQ ID NO 2
<211> LENGTH: 1953
<212> TYPE: DNA
<213> ORGANISM: Candida tropicalis

<400> SEQUENCE: 2

```
atgtcaggat tagaaattgc tgcagctgcc gttcttggta gtcagttatt agaagccaaa      60
tatttaattt ccgatgatgt actgttggcc aaaacagttg ctcttaatgc acttccatat     120
ttatggaaag cctccagggg taaagcttca tattggtatt tctttgaaaa atcagtattt     180
aaaaatccaa ataataaagc attggcattt ccaagaccaa gaagaatgc accaccacca      240
aaggttgatg atgaaggatt tcaaatttat gacgatcaat ttgacctaga agaatatacc     300
tataaggaat tgtatgacat ggttttgaaa tactcttaca ttttgaaaca tgaatatggt     360
gttactgcaa atgatactat tggtgttcct tgtatgaata aaccactttt cattgtttta     420
tggttggcct tatggaatat tggtgccttg ccagcatttt tgaatttcaa caccaaagat     480
aaaccattga ttcactgtct taaattgtc aatgctagtc aagttttcgt tgatcctgat     540
tgtgatgctc aatcaaaga tactgaatct caaattaaag aggaattacc acatgttaga     600
ataaattaca ttgatgaatt tgctttgttt gatagattaa gactcaagtc tactccaaaa     660
tacagagctg aagatagtac tagaagacca acagatacgg attcttccgc ctgtgcgttg     720
```

| | |
|---|---|
| atctatacat caggtaccac tggtttacca aaagcaggta tcatgtcttg agaaaagca | 780 |
| ttcatggctt ctgttttctt tggccatatt atgaaaatta agaatgattc caatgtttta | 840 |
| acagctatgc cattgtatca ttcaacagct gctatgttgg gtttgtgtcc tactttaatt | 900 |
| gttggtggtt gtgtttctgt ttctcaaaaa ttctcagcca cttcattctg gactcaagct | 960 |
| agattatgtg gtgccacaca tattcaatat gttggtgaag tttgtcgtta tttgttaaac | 1020 |
| tcaaaacatc acccagatca agatagacac aatgttaaaa ttgcctatgg taatggatta | 1080 |
| cgtccagata tatggtctga attcaagaga agattccaca ttgaaggtat tggggaattt | 1140 |
| tatgcagcta ctgaatctcc aattgccact acaaacttac aatacggtga atatggtgta | 1200 |
| ggtgcctgtc gtaaatatgg ttcacttatt agtttattgt tatctaccca acaaaaattg | 1260 |
| gccaagatgg atccagaaga tgaaagtgaa atttataagg atccaaaaac tggattttgt | 1320 |
| gttgaagctg catataatga acctggtgaa ttgttgatga gaattttaaa tcctaatgat | 1380 |
| attcaaaaat cattccaagg ttattatggt aacaaatctg ctaccaatag caaaattctc | 1440 |
| acgaatgttt tcaaaaagg gatgcttggt atagaagtg tgacttgtt gaaaatggat | 1500 |
| gaacatcaat tgttgtattt tgttgataga ttgggtgata ccttccgttg gaaatcagaa | 1560 |
| aatgtttcag caactgaagt tgaaaatgag ttgatgggat ctaaagcatt gaaacaatct | 1620 |
| gttgttgttg gtgttaaagt tccaaatcac gaaggtagag cttgttttgc tgtatgtgaa | 1680 |
| gcaaagatg atttaactca tgaagatatt ttgaaattga ttcatggaca tgttactaaa | 1740 |
| tcgttaccag tttatgcaca acctgcattc attaaaatcg gatccattga agcttctcat | 1800 |
| aatcataaag ttccaaagaa tcaatttaag aatcaaaaat taccaaaagg tgaagatggt | 1860 |
| aaagacttga tttactggtt gaatggtgat aaatatcaag agttgactga agaggattgg | 1920 |
| tctttgatct gtactggtaa agccaaattg taa | 1953 |

<210> SEQ ID NO 3
<211> LENGTH: 4455
<212> TYPE: DNA
<213> ORGANISM: Candida tropicalis

<400> SEQUENCE: 3

| | |
|---|---|
| atgggagaaa taaccccaac tgacaaaagc gaagaccagt caatggttaa tgcatatcat | 60 |
| ggatttgata ctcatgcatc agaagatata caagatttag ccaaaacttt tactcatcat | 120 |
| tcaattggcg atggtactga tggtttacaa agatatctta caaatatgac agaagtacca | 180 |
| ggtataaatc cttacaccga agatatttac actagtgacc aattgaatcc agactcagat | 240 |
| aattttaatg caaagttttg gatcaagaac ttgagaaaat tgtatgattc agatccagat | 300 |
| tattacaagc catcaagatt gggagttgcc tatagagatt taagagctta tggtgtggcc | 360 |
| aatgattctg attaccagcc cactgtggca aacgcggtct ggaagtttat caagagggga | 420 |
| ttgcattatt tagaaaaagg tgatggctca aggtattttg atattttaaa atcaatggat | 480 |
| ggaataatga accaggtga acttacagtt gttttaggta gaccagggc tggttgttcc | 540 |
| acattgttga aaacattggc ttcacaaaca tatggatttc atattggaaa agaatcaaaa | 600 |
| atcagttatg atggtttaac tcctcccgaa atcgaaaaaa cttatagggg taatgttgta | 660 |
| tactctgcag aaacagatgt tcattttcca catttgactg tcggacaagt cttggaattt | 720 |
| gctgctagaa tgagaacgcc acagaacaga ggtgaaggtg tagatagaga acatatgcc | 780 |
| aaacaccttg ctagtgttta tatggctact tatgggttat ctcatacaag aaataccaat | 840 |
| gtgggtaacg attttgtcag aggagtttct ggtggtgaaa gaaaaagggt ctccattgct | 900 |

```
gaagtttcgt tgagtggtgc aaatgttcaa tgttgggata atgccactag aggtttggat      960
gctgcaaccg cattggaatt catcagagca ttgaagactt ctgctgctat tttggaaagt     1020
accccattga ttgctattta tcaatgttca caagatgctt atgacttgtt tgataatgtt     1080
gtcgttttgt atgaaggttt ccaaattttt tttggtaaag ccaataaagc caaggagtat     1140
tttgtaaaca tgggatacaa gtgtcctcaa agacaaacca ctgctgactt tttaacttca     1200
ttgactaatc cagctgaaag agagccatta ccaggttatg agaataaagt cccaaggact     1260
cctcaagaat tgaagcata ttggaagaaa tccccagagt atactgcatt ggttaatgaa      1320
attgattcat atttcattga gtgtgagaaa ttaaacacca gacaactcta ccaagattca     1380
catgttgcaa gacaatccaa caatattcgt ccatcttcac catatactgt atcatttttc     1440
atgcaagtaa agtatgttat acaaagaaat ttcctccgta tgaaagctga tccatcgatt     1500
ccgttgacta ctattttctc acaactagtt atgggactta ttcttgcctc ggtattttac     1560
aatcttcctg caacttcagg ttcttttttac taccgatccg gtgcgcttta ctttggtttg     1620
ttatttaatg ctatttcgtc cctacttgaa attattgccc ttttttgaagc aagacccatt     1680
gttgagaaac ataaaaaata tgccctttat cgtccatcag cagatgcatt agcaagtatt     1740
ataagtgagt taccagttaa gttttttcaa tccttgtgtt tcaacattcc tttctatttt     1800
atggttaacc ttagaagaga tgctggtaga ttcttctttt attggttaat tggtatatta     1860
ggtacattca ttatgtcaca cttattcaga tctattggtg cagtatttac tactttagca     1920
ggtgctatga ctccggcggg ggtgatttta ttagcaatga tattatttgc tggatttgtc     1980
attccatttc caagcatgtt gggttggtct aaatggataa aatggataaa tcctgtcact     2040
tatttgtttg aatcacttat ggtaaacgag tatcataata gagagtttga atgcagtgat     2100
ttcgtaccta tgggaccagg atatgagaat cttagtcttg aaaataaggt ttgttcaagt     2160
ttgggtggca tccctggtag tgcttttgtt caaggtgatg attatttaag acttggatttt    2220
gcctttttcta actcccataa gtggagaaat tttggtatat ctgttgcgtt tgctgtgttt     2280
cttttgtttc tttatgttgc attgactgaa ctcaataaag gtgctatgca aaaaggtgaa     2340
attgtgttgt tcttagagg atctttgaag aaatacaaga gaaactccag tagcgcagat      2400
attgaatccg gtaaagaaat agtgaaattt aatttccaag acgaagcaga atcttctaat     2460
agtgatcgta ttgatgaaaa gggttctacg ggcagtgaag aattactacc agacaacaga     2520
gaaattttct tttggaagaa tttgacatat caagtcaaga ttaagaaaga agatagagtc     2580
attttagacc atgttgatgg ttgggttaaa ccaggtcaaa ttactgcatt gatgggtgca     2640
tctggtgctg gtaagaccac tttgttgaat tgtttatctg agagagtaac tactggtgtt     2700
attactgatg gtgtgagaat ggttaatggt catgcgttag attcttcgtt ccaaagatca     2760
attggttatg tgcaacaaca agatgttcat ttacagacat ctacagttag agaagcgttg     2820
caattctccg catatttgag acaatcaaac aaaatatcta agaaggagaa ggatgaatat     2880
gttgactacg tcattgactt gttggagatg actaactatg cggatgcatt ggttggtgtt     2940
gccggtgaag gtttgaatgt tgaacaaaga aagagattaa ccatcggtgt tgaattagtt     3000
gccaagccta agttgttact attccttgat gaaccaactt ctggtttaga ctcccaaact     3060
gcctggtcta tttgtaagtt gatgagaaag ttagctgatc atggtcaagc tatcttgtgt     3120
acaattcatc aaccttccgc acttattatg gctgaattcg atagattgtt gttttttgcaa    3180
aagggtggta gaactgctta ttttggtgac ttgggtaaaa actgtcaaac catgattgac     3240
```

```
tactttgaaa aacacggagc agatccatgt cccaaagaag ccaatccagc agaatggatg    3300
ttggaagttg ttggtgccgc tccaggctcc catgctaaac aggactattt tgaagtttgg    3360
agaaactctg acgaatatag agctgttcaa aatgaaatca cccatatgga aactgaatta    3420
gttaaattac aagagatgaa agatcccgaa gcacttttga aatacgctgc acccatttgg    3480
aaacaatatt tgcttgttag ttggagggcg attgtacaag attggagatc acctggatat    3540
atatactcca aattttctt gattatcgtg tcatctatat tgattggatt ttcattttt    3600 aaagccaaaa atacagttca agggttgacg aatcaaatgc ttgctatatt tatgttcaca    3660
gttcaattca caactattat tgaccaaatg ttgccatttt tgttcgaca acgtgaggtg    3720 tatgaggtta gagaagcacc ttccagaaca tatagttggg ttgccttcat tacaggtcaa    3780
ataacttcag agcttcctta tcaaataatt gttggaacga ttgctttctt ctgctggtac    3840
tatcctgttg gattatatac caatgctgaa cctacacata gtgtgactga acgtggtgcc    3900
ttgatgtggt tgtttattac ttcattttt gtttacacat caacatttgg tcaattatgt    3960
atgtcattca atgaagatat tgaaaatgct ggaactgttg ctgctacatt attcaccttg    4020
tgtttgatat tttgtggtgt tatggttgtt ccagagaata tgccacgatt ttggattttc    4080
atgtacagat gtaatccatt tacttatatg attcaaggtg ttctttcaac gggattagct    4140
cgcaataaag ttgtttgtgc tgcaagagaa cttgttctgc ttcaaccacc aaaaggtcaa    4200
acttgttctt cattcttgga tcctatatc agtgtggctg gaggttatta tttacctaat    4260
aatgatggaa cttgttcatt ctgttcagta gataatactg atatgttttt acatcgtatc    4320
catgccttat acagtgagag atggagaaat tttggattat ttattacatt cattgtgatt    4380
aatgttgtct tgactgtatt cttttattgg ttagctaggg taccaaaagg gtcaagatca    4440
aagactaaaa agtga    4455

<210> SEQ ID NO 4
<211> LENGTH: 1372
<212> TYPE: DNA
<213> ORGANISM: Candida tropicalis

<400> SEQUENCE: 4
aagagatttc ttgtattcat tacaattatt acatggttga aaactgtatc aactgctcat      60
attcctgcac cacttgctga tccaagtaga gatgagtttt atactccatc tccaggtttt     120
gaatacgcta ctccaggaac tatttttaaa atccgtccaa ctcctcgtgc tgttcgtaat     180
ttattattct ttcatgttcc tttaaaaaac tcttggcaat tgttggttag atctcaagat     240
tcttttggtg aacctaatgc tatagttact acaattcttg aacctatgaa ttcaaatcct     300
tcaaaaattt tatcttatca aactttgaa gattcaactt cattaaaatg cgctaccagt     360
tataattatc aagttggtat tccaccattt ggaaatgttg ctacccaatt tgaaatgaaa     420
tttataattc ctgctttaaa taaggatat tttgtaatta gtcctgatta tgaaggacca     480
agaggtgcat ttactgttgg tgcacaagca gcacatgcag tattggattc tattcgtgct     540
gtattgaatt ctgggtctat aacttctatt gatccagatg ctaaagttgc aatgtggggt     600
tattctggag atccttagc atcaagttgg gcagctgtaa tgcaacctga atatgcacct     660
gaattgtcaa ataatttaat aggtgttgcc ttggggagga tttgttacta atataactgc     720
tgttgctgaa tattctgata gaactccact ttctggtctt gttccagtag cacttaatgg     780
attagccaat gaatatccat tggttagaca attgcttaat caagaaataa gtcctaaaaa     840
aaatgcaagt tttcatcgtg gagttcaaaa atgttttctt cctgctatag cttattttag     900
```

```
aggaagaact attcttggta gaaataatga aaagaaagca atgtttccta atggatggca      960
tttacttgat aatcccggat ttttttgaaa ttcttgataa aaataatttg atttcttata     1020
acgcaattcc aaaaattcca atatttgtat atcatggaac aaaaaagatg gagttgttcc     1080
gatttcctat gctcataaaa ttttcgataa atggtgtgat gagggaattg aatcgtttga     1140
atttgcagaa tctttaacta ctggacatat attggaaact tttactggtg ctgcagccgc     1200
ttggacttgg ttacaaaaac gatttgatga tgtacctcca tataatggtt gtttccatac     1260
aagaagactc actaatttga agtacacggg agcatcaaag agtataattg attattacga     1320
tgggttgttt aaagaaagct tcactgtgaa gaatagtacc tatcttgtct ag              1372

<210> SEQ ID NO 5
<211> LENGTH: 1960
<212> TYPE: DNA
<213> ORGANISM: Candida tropicalis

<400> SEQUENCE: 5
atgtcaggat tagaaattgc tgcagctgcc gttcttggta gtcagttatt agaagccaaa       60
tatttaattt ccgatgatgt actgttggcc aaaacagttg ctcttaatgc acttccatat      120
ttatggaaag cctccagggg taaagcttca tattggtatt tctttgaaaa atcagtattt      180
aaaaatccaa ataataaagc attggcattt ccaagaccaa gaaagaatgc accaccacca      240
aaggttgatg atgaaggatt tcaaatttat gacgatcaat ttgacctaga agaatatacc      300
tataaggaat gtatgacat ggttttgaaa tactcttaca ttttgaaaca tgaatatggt       360
gttactgcaa atgatactat tggtgtttct tgtatgaata aaccactttt cattgtttta      420
tggttggcct tatggaatat tggtgccttg ccagcatttt tgaatttcaa caccaaagat      480
aaaccattga ttcactgtct taaaattgtc aatgctagtc aagttttcgt tgatcctgat      540
tgtgatgctc caatcaaaga tactgaatct caaattaaag aggaattacc acatgttaga      600
ataaattaca ttgatgaatt tgctttgtat tgatagatta agactcaagt ctactccaaa      660
atacagagct gaagatagta ctagaagacc aacagatacc gattcttccg cctgtgcgtt      720
gatctataca tcaggtacca ctggtttacc aaaagcaggt atcatgtctt ggagaaaagc      780
attcatggct tctgtttcct ttggccatat tatgaaaatt aagaatgatt ccaatgttt       840 tacagttatg ccattgtatc attcaacagc tgctatgttg ggtttgtgtc ctactttaat      900
tgttggtggt tgtgtttctg tttctcaaaa attctcagcc acttcattct ggactcaagc      960
tagattatgt ggtgccacac atattcaata tgttggtgaa gtttgtcgtt atttgttaaa     1020
ctcaaaacat cacccagatc aagatagaca caatgttaaa attgcctatg gtaatggatt     1080
acgtccagat atatggtctg aattcaagag aagattccac attgaaggta ttggggaatt     1140
ttatgcagct actgaatctc caattgccac tacaaactta caatacggtg aatatggtgt     1200
aggtgcctgt cgtaaatatg gttcacttac tagtttattg ttatctaccc aacaaaaatt     1260
ggccaagatg gatccagaag atgaaagtga aatttataag gatccaaaaa ctggattttg     1320
tgttgaagct gcatataatg aacctggtga attgttgatg agaattttaa atcctaatga     1380
tattcaaaaa tcattccaag gttattatgg taacaaatct gctaccaata gcaaaattct     1440
cacgaatgtt ttcaaaaaag gagatgcttg gtatagaagt ggtgacttgt tgaaaatgga     1500
tgaacatcaa ttgttgtatt ttgttgatag attgggtgag aaataccttc cgttggaaat     1560
cagaaaatgt ttcagcaact gaagttgaaa atgagttgat gggatctaaa gcattgaaac     1620
```

```
aatctgttgt tgttggtgtt aaagttccag gaatcacgaa ggtagagctt gttttgctgt      1680
atgtgaagca aaagatgatt taactcatga agatattttg aaattgattc atggacatgt      1740
tactaaatcg ttaccagttt atgcacaacc tgcattcatt aaaatcggat ccattgaagc      1800
ttctcataat cataaagttc caagaatca atttaagaat caaaaattac caaaaggtga       1860
agatggtaaa gacttgattt actggttgaa tggtgataaa tatcaagagt tgactgaaga      1920
ggattggtct tgatctgta ctggtaaagc caaattgtaa                              1960
```

<210> SEQ ID NO 6
<211> LENGTH: 4455
<212> TYPE: DNA
<213> ORGANISM: Candida tropicalis
<400> SEQUENCE: 6

```
atgggagaaa taaccccaac tgacaaaagc gaagaccagt caatggttaa tgcatatcat        60
ggatttgata ctcatgcatc agaagatata caagatttag ccaaaacttt tactcatcat       120
tcaattggcg atggtactga tggtttacaa agatatctta caaatatgac agaagtacca       180
ggtataaatc cttacaccga agatatttac actagtgacc aattgaatcc agactcagat       240
aattttaatg caaagttttg gatcaagaac ttgagaaaat tgtatgattc agatccagat       300
tattacaagc catcaagatt gggagttgcc tatagagatt taagagctta tggtgtggcc       360
aatgattctg attaccagcc cactgtggca acgcgggtct ggaagtttat caagagggga      420
ttgcattatt tagaaaaagg tgatggctca aggtattttg atattttaaa atcaatggat       480
ggaataatga aaccaggtga acttacagtt gttttaggta gaccaggggc tggttgttcc       540
acattgttga aaacattggc ttcacaaaca tatggatttc atattggaaa agaatcaaaa       600
atcagttatg atggtttaac tcctcccgaa atcgaaaaaa cttataggg taatgttgta        660 tactctgcag aaacagatgt tcattttcca catttgactg tcggacaagt cttggaattt       720
gctgctagaa tgaaacgcc acagaacaga gtgaaggtg tagatagaga acatatgcc         780 aaacaccatg ttagtgttta tatggctact tatgggttat ctcatacaag aaataccaat       840
gtgggtaacg atttgtcag aggagtttct ggtggtgaaa gaaaaagggt ctccattgct        900
gaagtttcgt tgagtggtgc aaacgttcaa tgttgggata atgccactaa aggtttggat       960
gctgcaaccg cattgaatt catcagagca ttgaagactt ctgctgctat tttggaaagt       1020
accccattga ttgctactta tcaatgttca caagatgctt atgacttgta tgataatgct      1080
gtcgttttgt atgaaggttt ccaaattttt tttggtaaag ccaataaagc caaggagtat      1140
tttgtaaaca tgggatacaa gtgtcctcat agacaaaaca ctgctgactt tttaacttca      1200
ttgactaatc cagctgaaag agagccatta ccaggttatg agaataaagt cccaaggact      1260
cctcaagaat tgaagcata ttggaagaaa tccccagagt atactgcatt ggttaatgaa       1320
attcattcat atttcattga gtgtgagaaa ttaaacacca gacaactcta ccaagattca      1380
catgttgcaa gacaatccaa caatattcgt ccatcttcac catatactgt atcattttc       1440 atgcaagtaa agtatgttat acaaagaaat ttcctccgta tgaaagctga tccatcgatt      1500
ccgttgacta ctattttctc acaactagtt atgggactta ttcttgcctc ggtattttac      1560
aatcttcctg caacttcagg ttcttttac taccgatccg gtgcgcttta ctttggtttg       1620
ttatttaatg ctatttcgtc cctacttgaa attattgccc ttttgaagc aagacccatt      1680 gttgagaaac ataaaaaata tgcccttat cgtccatcag cagatgcatt agcaagtatt      1740
ataagtgagt taccagttaa gttttttcaa tccttgtgtt tcaacattcc tttctatttt    1800
```

```
atggttaacc ttagaagaga tgctggtaga ttcttctttt attggttaat tggtatatta    1860
ggtacattca ttatgtcaca cttattcaga tctattggtg cagtatttac tactttagca    1920
ggtgctatga ctccggcggg ggtgatttta ttagcaatga tattatttgc tggatttgtc    1980
attccatttc caagcatgtt gggttggtct aaatggataa aatggataaa tcctgtcact    2040
tatttgtttg aatcacttat ggtaaacgag tatcataata gagagtttga atgcagtgat    2100
ttcgtaccta tgggaccagg atatgagaat cttagtcttg aaaataaggt ttgttcaagt    2160
ttgggtggca tccctggtag tgcttttgtt caaggtgatg attatttaag acttggattt    2220
gccttttcta actcccataa gtggagaaat tttggtatat ctgttgcgtt tgctgtgttt    2280
cttttgtttc tttatgttgc attgactgaa ctcaataaag gtgctatgca aaaggtgaa    2340 attgtgttgt tcttagagg atcttttgaag aaatacaaga gaaactccag tagcgcagat    2400
attgaatccg gtaaagaaat agtgaaattt aatttccaag acgaagcaga atcttctaat    2460
agtgatcgta ttgatgaaaa gggttctacg ggcagtgaag aattactacc agacaacaga    2520
gaaattttct tttggaagaa tttgacatat caagtcaaga ttaagaaaga gatagagtc    2580 atttagacc atgttgatgg ttgggttaaa ccaggtcaaa ttactgcatt gatgggtgca    2640
tctggtgctg gtaagaccac tttgttgaat tgtttatctg agagagtaac tactggtgtt    2700
attactgatg gtgtgagaat ggttaatggt catgcgttag attcttcgtt ccaaagatca    2760
attggttatg tgcaacaaca agatgttcat ttacagacat ctacagttag agaagcgttg    2820
caattctccg catatttgag acaatcaaac aaaatatcta agaaggagaa ggatgaatat    2880
gttgactacg tcattgactt gttggagatg actaactatg cggatgcatt ggttggtgtt    2940
gccggtgaag gtttgaatgt tgaacaaaga aagagattaa ccatcggtgt tgaattagtt    3000
gccaagccta agttgttact attcttggat gaaccaactt ctggtttaga ctcccaaact    3060
gcctggtcta tttgtaagtt gatgagaaag ttagctgatc atggtcaagc tatcttgtgt    3120
acaattcatc aaccttccgc acttattatg gctgaattcg atagattgtt gttttgcaa    3180 aagggtggta gaactgctta ttttggtgac ttgggtaaaa actgtcaaac catgattgac    3240
tactttgaaa aacacggagc agatccatgt cccaaagaag ccaatccagc agaatggatg    3300
ttggaagttg ttggtgccgc tccaggctcc catgctaaac aggactattt tgaagtttgg    3360
agaaactctg acgaatatag agctgttcaa aatgaaatca cccatatgga aactgaatta    3420
gttaaattac caagagatga agatcccgaa gcacttttga aatacgctgc acccatttgg    3480
aaacaatatt tgcttgttag ttggagggcg attgtacaag attggagatc acctggatat    3540
atatactcca aatttttctt gattatcgtg tcatctatat tgattggatt ttcatttttt    3600
aaagccaaaa atacagttca agggttgacg aatcaaatgc ttgctatatt tatgttcaca    3660
gttcaattca caactattat tgaccaaatg ttgccatttt ttgttcgaca acgtgaggtg    3720
tatgaggtta gagaagcacc ttccagaaca tatagttggg ttgccttcat tacaggtcaa    3780
ataacttcag agcttcctta tcaaataatt gttggaacga ttgctttctt ctgctggtac    3840
tatcctgttg gattatatac caatgctgaa cctacacata gtgtgactga acgtggtgcc    3900
ttgatgtggt tgtttattac ttcatttttt gtttacacat caacatttgg tcaattatgt    3960
atgtcattca atgaagatat tgaaaatgct ggaactgttg ctgctacatt attcaccttg    4020
tgtttgatat tttgtggtgt tatggttgtt ccagagaata tgccacgatt ttggattttc    4080
atgtacagat gtaatccatt tacttatatg attcaaggtg ttctttcaac gggattagct    4140
```

```
cgcaataaag ttgtttgtgc tgcaagagaa cttgttctgc ttcaaccacc aaaaggtcaa    4200
acttgttctt cattcttgga tccttatatc agtgtggctg gaggttatta tttacctaat    4260
aatgatggaa cttgttcatt ctgttcagta gataatactg atatgttttt acatcgtatc    4320
catgccttat acagtgagag atggagaaat tttggattat ttattacatt cattgtgatt    4380
aatgttgtct tgactgtatt cttttattgg ttagctaggg taccaaaagg gtcaagatca    4440
aagactaaaa agtga                                                     4455
```

```
<210> SEQ ID NO 7
<211> LENGTH: 31
<212> TYPE: DNA
<213> ORGANISM: Artificial Sequence
<220> FEATURE:
<223> OTHER INFORMATION: ADHpro_F

<400> SEQUENCE: 7
aaactcgagt ctagctccct aacatgtagg t                                   31

<210> SEQ ID NO 8
<211> LENGTH: 35
<212> TYPE: DNA
<213> ORGANISM: Artificial Sequence
<220> FEATURE:
<223> OTHER INFORMATION: ADHpro_R

<400> SEQUENCE: 8
aaagtcgaca gttgattgta tgcttggtat agctt                               35

<210> SEQ ID NO 9
<211> LENGTH: 46
<212> TYPE: DNA
<213> ORGANISM: Artificial Sequence
<220> FEATURE:
<223> OTHER INFORMATION: ADHter_F

<400> SEQUENCE: 9
aaagtcgact ctagataagc gaatttctta tgatttatga ttttta                   46

<210> SEQ ID NO 10
<211> LENGTH: 34
<212> TYPE: DNA
<213> ORGANISM: Artificial Sequence
<220> FEATURE:
<223> OTHER INFORMATION: ADHter_R

<400> SEQUENCE: 10
aaagcggccg cgtgtggaag aacgattaca acag                                34

<210> SEQ ID NO 11
<211> LENGTH: 53
<212> TYPE: DNA
<213> ORGANISM: Artificial Sequence
<220> FEATURE:
<223> OTHER INFORMATION: LIP1_F

<400> SEQUENCE: 11
aaagtcgaca tgagatttct tgtattcatt acaattatta catggttgaa aac           53

<210> SEQ ID NO 12
<211> LENGTH: 61
<212> TYPE: DNA
<213> ORGANISM: Artificial Sequence
<220> FEATURE:
<223> OTHER INFORMATION: LIP1_R
```

<400> SEQUENCE: 12
aaatctagag tggtggtggt ggtggtggac aagataggta ctattcttca cagtgaagct    60
t                                                                    61

<210> SEQ ID NO 13
<211> LENGTH: 39
<212> TYPE: DNA
<213> ORGANISM: Artificial Sequence
<220> FEATURE:
<223> OTHER INFORMATION: FAT1_F

<400> SEQUENCE: 13
aaagtcgaca tgtcaggatt agaaattgct gcagctgcc                            39

<210> SEQ ID NO 14
<211> LENGTH: 42
<212> TYPE: DNA
<213> ORGANISM: Artificial Sequence
<220> FEATURE:
<223> OTHER INFORMATION: FAT1_R

<400> SEQUENCE: 14
aaatctagac aatttggctt taccagtaca gatcaaagac ca                        42

<210> SEQ ID NO 15
<211> LENGTH: 40
<212> TYPE: DNA
<213> ORGANISM: Artificial Sequence
<220> FEATURE:
<223> OTHER INFORMATION: MRP1_F

<400> SEQUENCE: 15
aaagtcgaca tgggagaaat aaccccaact gacaaaagcg                           40

<210> SEQ ID NO 16
<211> LENGTH: 36
<212> TYPE: DNA
<213> ORGANISM: Artificial Sequence
<220> FEATURE:
<223> OTHER INFORMATION: MRP1_R

<400> SEQUENCE: 16
aaatctagac tttttagtct tgacccttttt ggtacc                              36

<210> SEQ ID NO 17
<211> LENGTH: 31
<212> TYPE: DNA
<213> ORGANISM: Artificial Sequence
<220> FEATURE:
<223> OTHER INFORMATION: P1_F

<400> SEQUENCE: 17
aaaggatcct ctagctccct aacatgtagg t                                    31

<210> SEQ ID NO 18
<211> LENGTH: 35
<212> TYPE: DNA
<213> ORGANISM: Artificial Sequence
<220> FEATURE:
<223> OTHER INFORMATION: P1_R

<400> SEQUENCE: 18
aaagtcgaca gttgattgta tgcttggtat agctt                                35

<210> SEQ ID NO 19
<211> LENGTH: 37
<212> TYPE: DNA
<213> ORGANISM: Artificial Sequence
<220> FEATURE:
<223> OTHER INFORMATION: P2_F

<400> SEQUENCE: 19
aaagtcgacc acgtgtctag ctccctaaca tgtaggt        37

<210> SEQ ID NO 20
<211> LENGTH: 37
<212> TYPE: DNA
<213> ORGANISM: Artificial Sequence
<220> FEATURE:
<223> OTHER INFORMATION: P2_R

<400> SEQUENCE: 20
aaagcggccg cagttgattg tatgcttggt atagctt        37

<210> SEQ ID NO 21
<211> LENGTH: 40
<212> TYPE: DNA
<213> ORGANISM: Artificial Sequence
<220> FEATURE:
<223> OTHER INFORMATION: P3_F

<400> SEQUENCE: 21
aaagtcgact aagcgaattt cttatgattt atgattttta        40

<210> SEQ ID NO 22
<211> LENGTH: 32
<212> TYPE: DNA
<213> ORGANISM: Artificial Sequence
<220> FEATURE:
<223> OTHER INFORMATION: P3_R

<400> SEQUENCE: 22
aaacacgtgg tgtggaagaa cgattacaac ag        32

<210> SEQ ID NO 23
<211> LENGTH: 59
<212> TYPE: DNA
<213> ORGANISM: Artificial Sequence
<220> FEATURE:
<223> OTHER INFORMATION: P4_F

<400> SEQUENCE: 23
cagttgattg tatgcttggt atagtcgaca tgagatttct tgtattcatt acaattatt        59

<210> SEQ ID NO 24
<211> LENGTH: 54
<212> TYPE: DNA
<213> ORGANISM: Artificial Sequence
<220> FEATURE:
<223> OTHER INFORMATION: P4_R

<400> SEQUENCE: 24
gttaactaag cgaatttctt atgatttatg tcgacagtgg tggtggtggt ggtg        54

<210> SEQ ID NO 25
<211> LENGTH: 56
<212> TYPE: DNA
<213> ORGANISM: Artificial Sequence
<220> FEATURE:
<223> OTHER INFORMATION: P5_F

<400> SEQUENCE: 25
cagttgattg tatgcttggt atagcgggcc gcatgtcagg attagaaatt gctgca        56

<210> SEQ ID NO 26
<211> LENGTH: 61
<212> TYPE: DNA
<213> ORGANISM: Artificial Sequence
<220> FEATURE:
<223> OTHER INFORMATION: P5_R

<400> SEQUENCE: 26
gttaactaag cgaatttctt atgatttatg cggccgcaca atttggcttt accagtacag    60
a                                                                    61

<210> SEQ ID NO 27
<211> LENGTH: 43
<212> TYPE: DNA
<213> ORGANISM: Artificial Sequence
<220> FEATURE:
<223> OTHER INFORMATION: P6_F

<400> SEQUENCE: 27
aaagcggccg cataagcgaa tttcttatga tttatgattt tta                      43

<210> SEQ ID NO 28
<211> LENGTH: 41
<212> TYPE: DNA
<213> ORGANISM: Artificial Sequence
<220> FEATURE:
<223> OTHER INFORMATION: P6_R

<400> SEQUENCE: 28
aaactcgagc acgtgagttg attgtatgct tggtatagct t                        41

<210> SEQ ID NO 29
<211> LENGTH: 40
<212> TYPE: DNA
<213> ORGANISM: Artificial Sequence
<220> FEATURE:
<223> OTHER INFORMATION: P7_F

<400> SEQUENCE: 29
aaacacgtgt aagcgaattt cttatgattt atgattttta                          40

<210> SEQ ID NO 30
<211> LENGTH: 32
<212> TYPE: DNA
<213> ORGANISM: Artificial Sequence
<220> FEATURE:
<223> OTHER INFORMATION: P7_R

<400> SEQUENCE: 30
aaactcgagg tgtggaagaa cgattacaac ag                                  32

<210> SEQ ID NO 31
<211> LENGTH: 52
<212> TYPE: DNA
<213> ORGANISM: Artificial Sequence
<220> FEATURE:
<223> OTHER INFORMATION: P8_F

<400> SEQUENCE: 31
cagttgattg tatgcttggt atagcacgtg atgggagaaa taaccccaac tg            52

```
<210> SEQ ID NO 32
<211> LENGTH: 59
<212> TYPE: DNA
<213> ORGANISM: Artificial Sequence
<220> FEATURE:
<223> OTHER INFORMATION: P8_R

<400> SEQUENCE: 32
gttaactaag cgaatttctt atgatttaca cgtgcttttt agtcttgacc cttttggta        59

<210> SEQ ID NO 33
<211> LENGTH: 56
<212> TYPE: DNA
<213> ORGANISM: Artificial Sequence
<220> FEATURE:
<223> OTHER INFORMATION: P9_F

<400> SEQUENCE: 33
gcttgatatc gaattcctgc agcccggggg atcctctagc tccctaacat gtaggt          56

<210> SEQ ID NO 34
<211> LENGTH: 55
<212> TYPE: DNA
<213> ORGANISM: Artificial Sequence
<220> FEATURE:
<223> OTHER INFORMATION: P9_R

<400> SEQUENCE: 34
ggggggcccg gtacccaatt cgccctctcg aggtgtggaa gaacgattac aacag           55
```